United States Patent [19]

Li et al.

[11] Patent Number: 5,703,244
[45] Date of Patent: Dec. 30, 1997

[54] PROCESS FOR PREPARATION OF CHIRAL 3-AMINO-PYRROLIDINE AND ANALOGOUS BICYCLIC COMPOUNDS

[75] Inventors: Qun Li, Libertyville; Wei-Bo Wang, Grayslake, both of Ill.; Daniel T. Chu, Santa Clara, Calif.; Lisa Anne Hasvold, Grayslake, Ill.

[73] Assignee: Abbott Laboratories, Abbott Park, Ill.

[21] Appl. No.: 754,641

[22] Filed: Nov. 21, 1996

[51] Int. Cl.[6] .................................. C07D 207/09
[52] U.S. Cl. ............................................. 548/557
[58] Field of Search ...................................... 548/557

[56] References Cited

U.S. PATENT DOCUMENTS

| | | | |
|---|---|---|---|
| 4,990,517 | 2/1991 | Petersen et al. | 514/224.5 |
| 5,059,597 | 10/1991 | Petersen et al. | 514/300 |
| 5,140,033 | 8/1992 | Schriewer et al. | 514/312 |

FOREIGN PATENT DOCUMENTS

| | | |
|---|---|---|
| 9116894 | 11/1991 | WIPO . |
| 9415939 | 7/1994 | WIPO . |
| 9510519 | 4/1995 | WIPO . |

*Primary Examiner*—Joseph McKane
*Attorney, Agent, or Firm*—Mona Anand

[57] ABSTRACT

A process for the preparation of chiral 3-aminopyrrolidine and analogous bicyclic derivatives from dihydroxy olefins by treatment with titanium isopropoxide, an optically active tartrate ester and tert-butyl hydroperoxide, followed by subsequent alkylation of the intermediate with an alkyl or alkenyl magnesium halide, then pyrrolidine ring formation by condensation with an arylmethylamine, subsequent chiral replacement of a ring hydroxyl group with an amino group with further protection thereof, optional additional substitution closing of the second ring, and hydrogenolysis to remove a ring-nitrogen protecting group.

8 Claims, No Drawings

PROCESS FOR PREPARATION OF CHIRAL 3-AMINO-PYRROLIDINE AND ANALOGOUS BICYCLIC COMPOUNDS

TECHNICAL FIELD

The present invention relates to a process for the preparation of chiral 3-amino-pyrrolidine derivatives which have use as intermediates in the preparation of certain pyrido[1,2-a]pyrimidine and quinolone antibacterial agents.

BACKGROUND OF THE INVENTION

The therapeutic use of certain pyrido[1,2-a]pyrimidine derivatives as antibacterial agents has been described in PCT patent applications WO 9116894, published Nov. 14, 1991, and WO 9510519, published Apr. 20, 1995. Quinolone antibacterial agents are well known and are described, for example, in U.S. Pat. Nos. 4,990,517; 5,140,033; 5,059,597; and PCT application WO 9415938.

More efficient processes for the preparation of key chiral intermediates for use in the synthesis of antibiotic agents are needed to ensure the ready availability of the compounds.

SUMMARY OF THE INVENTION

The present invention describes an efficient process for the enantioselective preparation of chiral 3-aminopyrrolidine, 2,7-diaza-bicyclo[3.3.0]octane, 2,8-diaza-bicyclo[4.3.0]nonane and 2,9-diaza-bicyclo[5.3.0]decane derivatives which have use as intermediates in the preparation of certain pyrido[1,2-a]pyrimidine and quinolone antibacterial agents.

In one aspect, the present invention relates to a process for the preparation of chiral 3-aminopyrrolidine compounds having the formula:

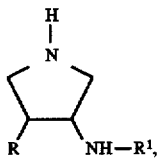

wherein R is $C_1$–$C_6$-alkyl, $C_2$–$C_6$-alkenyl, $C_2$–$C_6$-alkynyl, or $C_3$–$C_6$-cycloalkyl, and $R^1$ is hydrogen, $C_1$–$C_6$-alkyl or an amino-protecting group; the method comprising:

(a) protecting a single hydroxyl group of selected positional isomer of 2-butene-1,4-diol, by stepwise treatment with a base, an arylmethyl halide and a tetraalkyl-ammonium halide, and isolating a monoprotected hydroxy-olefin having the formula:

HO—CH$_2$—CH=CH—CH$_2$—O—CH$_2$-Ar wherein Ar represents the aryl moiety;

(b) chirally oxidizing the monoprotected hydroxy-olefin with titanium isopropoxide, an optically active chiral tartrate ester and t-butyl hydroperoxide, and isolating an epoxy compound having the formula:

(c) reacting the epoxy compound with an R—Mg—X compound, wherein R is as defined above, and X is halogen, under Grignard Reaction conditions, and isolating the chiral third intermediate compound having the formula:

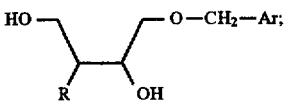

(d) removing the protecting group from the chiral third intermediate compound, and isolating the chiral fourth intermediate compound having the formula:

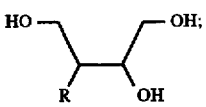

(e) sulfonylating the chiral fourth intermediate compound by treatment with a substituted sulfonyl chloride, and isolating the chiral diprotected triol compound having the formula:

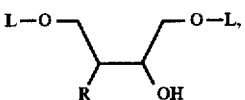

wherein L represents the substituted sulfonyl moiety;

(f) cyclizing the chiral diprotected triol compound by treatment with an arylmethylamine compound, as defined below, and isolating the chiral pyrrolidine intermediate having the formula:

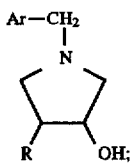

(g) replacing the hydroxyl group of the chiral pyrrolidine intermediate with an amino group by an amination reaction that inverts the chiral center, and isolating the chiral aminopyrrolidine compound having the formula:

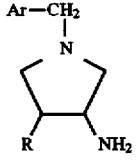

(h) derivatizing the amino group of the chiral aminopyrrolidine compound, and isolating the chiral substituted-aminopyrrolidine compound having the formula:

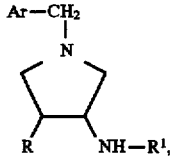

wherein $R^1$ is as defined above;

(i) deprotecting the ring nitrogen of the chiral substituted-aminopyrrolidine compound, and isolating the desired product.

In another aspect, the present invention relates to a process for the preparation of chiral compounds having the formula:

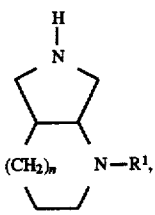

wherein n is 0, 1 or 2, and $R^1$ is hydrogen, $C_1$-$C_6$-alkyl or an amino-protecting group;

(a) protecting a single hydroxyl group of selected positional isomer of 2-butene-1,4-diol, by stepwise treatment with a base, an arylmethyl halide, and a tetraalkylammonium halide, and isolating a monoprotected hydroxy-olefin having the formula:

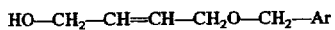

HO—CH$_2$—CH=CH—CH$_2$O—CH$_2$—Ar wherein Ar represents the aryl moiety;

(b) chirally oxidizing the monoprotected hydroxy-olefin with titanium isopropoxide, an optically active chiral tartrate ester and t-butyl hydroperoxide, and isolating an epoxy compound having the formula

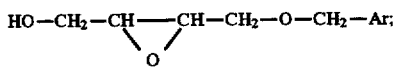

(c) reacting the epoxy compound with an $R^2$—Mg—X compound, wherein $R^2$ is vinyl, allyl or 3-butenyl, and X is halogen, under Grignard Reaction conditions, and isolating the chiral third intermediate compound having the formula:

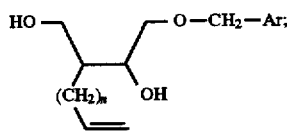

(d) removing the protecting group from the chiral third intermediate compound, and isolating the chiral fourth intermediate compound having the formula:

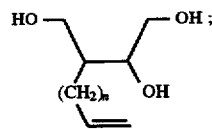

(e) sulfonylating the chiral fourth intermediate compound by treatment with a substituted sulfonyl chloride, and isolating the chiral diprotected triol compound having the formula:

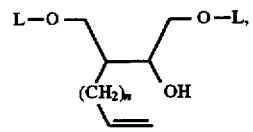

wherein L represents the substituted sulfonyl moiety;

(f) cyclizing the chiral diprotected triol compound by treatment with an arylmethylamine compound, and isolating the chiral pyrrolidine intermediate having the formula:

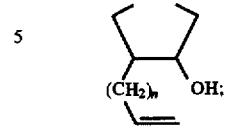

(g) replacing the hydroxyl group of the chiral pyrrolidine intermediate with an amino group by an amination reaction that inverts the chiral center, and isolating the chiral aminopyrrolidine compound having the formula:

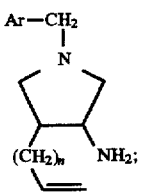

(h) derivatizing the amino group of the chiral aminopyrrolidine compound, and isolating the chiral substituted-aminopyrrolidine compound having the formula:

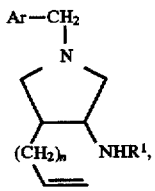

wherein $R^1$ is as defined above;

(i) oxidizing the chiral substituted-aminopyrrolidine compound with a hydroboration reagent, and isolating the chiral hydroxyalkyl compound having the formula:

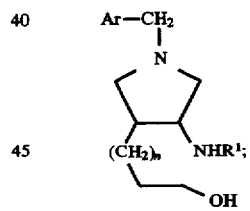

(j) reacting the chiral hydroxyalkyl compound with triphenylphosphine and diethylazobicarboxylate under Mitsunobu Reaction conditions in an aprotic solvent to obtain the compound having the formula:

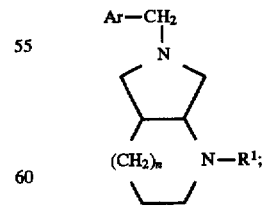

(k) deprotecting the ring nitrogen of the chiral bicyclic compound, and isolating the desired product.

The instant process for preparing these chiral intermediates from dihydroxy olefin compounds is more economical and more practical for large scale synthesis than the process for preparation of certain chiral 3-aminopyrrolidine derivatives described in PCT patent applications WO 9116894 (published Nov. 14, 1991) and WO 9510519 (published Apr. 20, 1995). One distinct advantage of the process of the invention over the published methods is that no large scale chiral chromatographic purifications are required.

DETAILED DESCRIPTION OF THE INVENTION

The term "$C_1$–$C_6$-alkyl" refers to saturated, straight- or branched-chain hydrocarbon radicals containing between one and six carbon atoms including, but not limited to, methyl, ethyl, propyl, i-propyl, n-butyl, tert-butyl, pentyl, neopentyl and hexyl.

The term "$C_2$–$C_6$-alkenyl", as used herein, refers to mono-unsaturated straight- or branched-chain hydrocarbon radicals containing from two to six carbon atoms including, but not limited to, vinyl, propenyl, n-butenyl, i-butenyl, n-pentenyl, and n-hexenyl.

The term "$C_2$–$C_6$-alkynyl", as used herein, refers to straight- or branched-chain hydrocarbon radicals possessing a single triple bond and containing from two to six carbon atoms including, but not limited to, ethynyl, propynyl, n-butynyl, n-pentynyl, and n-hexynyl.

The term "amino-protecting group", as used herein, refers to an easily removable group which is known in the art to protect an amino group against undesirable reaction during synthetic procedures and to be selectively removable. The use of amino-protecting groups is well known in the art for protecting groups against undesirable reactions during a synthetic procedure and many such protecting groups are known, cf, for example, T. H. Greene and P. G. M. Wuts, *Protective Groups in Organic Synthesis*, 2nd edition, John Wiley & Sons, New York (1991). Examples of amino-protecting groups include, but are not limited to, acyl groups, including acetyl, trifluoroacetyl, benzoyl and the like; acyloxy groups, including t-butyloxycarbonyl (BOC) and carbobenzyloxy, and the like.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick, et al., Vol. II, in the Techniques of Chemistry Series, John Wiley & Sons, NY, 1986.

The term "arylmethyl halide", as used herein, refers to a substituted or unsubstituted benzyl halide compound, including, but not limited to, benzyl bromide, benzyl chloride, benzyl iodide, 4-bromobenzyl bromide, 4-chlorobenzyl bromide, 4-methoxybenzyl bromide, and the like.

The term "$C_3$–$C_6$-cycloalkyl", as used herein, refers to saturated cyclic hydrocarbon radicals containing from three to six carbon atoms. Illustrative of $C_3$–$C_6$-cycloalkyl groups are cyclopropyl, cyclobutyl, cyclopentyl and cyclohexyl.

The term "halogen", as used herein, refers to chlorine, bromine, fluorine and iodine.

The term "optically active chiral tartrate ester", as used herein, refers to esters of D-(−)-tartaric or L-(+)-tartaric acid, such as for example, D-(−)-dimethyl tartrate, D-(−)-diethyl tartrate, D-(−)-diisopropyl tartrate, L-(+)-dimethyl tartrate, L-(+)-diethyl tartrate, L-(+)-diisopropyl tartrate, or the like.

The term "substituted sulfonyl chloride compound", refers to an alkyl or aryl substituted sulfonyl chloride, including, but not limited to, methanesulfonyl chloride, p-toluenesulfonyl chloride, benzenesulfonyl chloride and the like.

The term "tetraalkylammonium halide", as used herein, refers to the halide salts, such as chloride, fluoride, or bromide salts, of quaternary alkylammonium compounds wherein the alkyl moieties are selected from $C_1$–$C_6$-alkyl, as defined above, such as for example, tetramethylammonium chloride, tetrabutylammonium fluoride, tetraethylammonium bromide, tetrapropylammonium iodide, tetrapentylammonium chloride, tetrahexylammonium chloride, and the like.

Abbreviations which have been used in the descriptions of the schemes and the examples that follow are: BOC for t-butyloxycarbonyl; DEAD for diethylazodicarboxylate; DMF for dimethylformamide; DPPA for diphenylphosphoryl azide; LDA for lithium diisopropylamide; $Me_2S$ for dimethyl sulfide; $PPh_3$ for triphenylphosphine; THF for tetrahydrofuran.

The process of the invention for preparing 3-aminopyrrolidine derivatives may be applied selectively to prepare a specific chiral cis- or trans-isomer of the 3-aminopyrrolidine compounds.

Chiral cis-3-aminopyrrolidine derivatives may be obtained by the use of the cis-isomer of 2-butene-1,4-diol in step (a). The chiral cis-3-aminopyrrolidine having either the 3S,4S- or the 3R,4R-configuration may be obtained by varying the optically active tartrate ester referred to in step (b). Specifically, when the oxidation is performed with the assistance of the D-(−)-tartrate ester, the 3S,4S-product is obtained. Conversely, when the oxidation is performed with the assistance of the L-(+)-tartrate ester, the 3R,4R-product is obtained.

Chiral trans-3-aminopyrrolidine derivatives may be obtained by the use of the trans-isomer of 2-butene-1,4-diol in step (a) of the process. The specific chiral trans-3-aminopyrrolidine having either the 3S,4R- or the 3R,4S-configuration may subsequently be obtained by varying the optically active tartrate ester referred to in step (b) of the process. Specifically, when the oxidation is performed with the assistance of the L-(+)-tartrate ester, the 3S,4R-product is obtained. Conversely, when the oxidation is performed with the assistance of the D-(−)-tartrate ester, the 3R,4S-product is obtained.

The present process utilizes the Sharpless reaction (e.g., K. B. Sharpless, et at., J. Org. Chem., 51:1922–1925 (1986) and J. Amer. Chem. Soc., 102:5974–5976, (1980)) to perform chiral oxidation of olefins, with subsequent manipulation of the chiral oxidation products and conversion into the desired chiral antibacterial intermediates.

The process of the invention for obtaining specific chiral cis- and trans-isomers of the desired 3-aminopyrrolidine compounds may be better understood by reference to the reaction Schemes 1 and 2 illustrated below.

Scheme 1

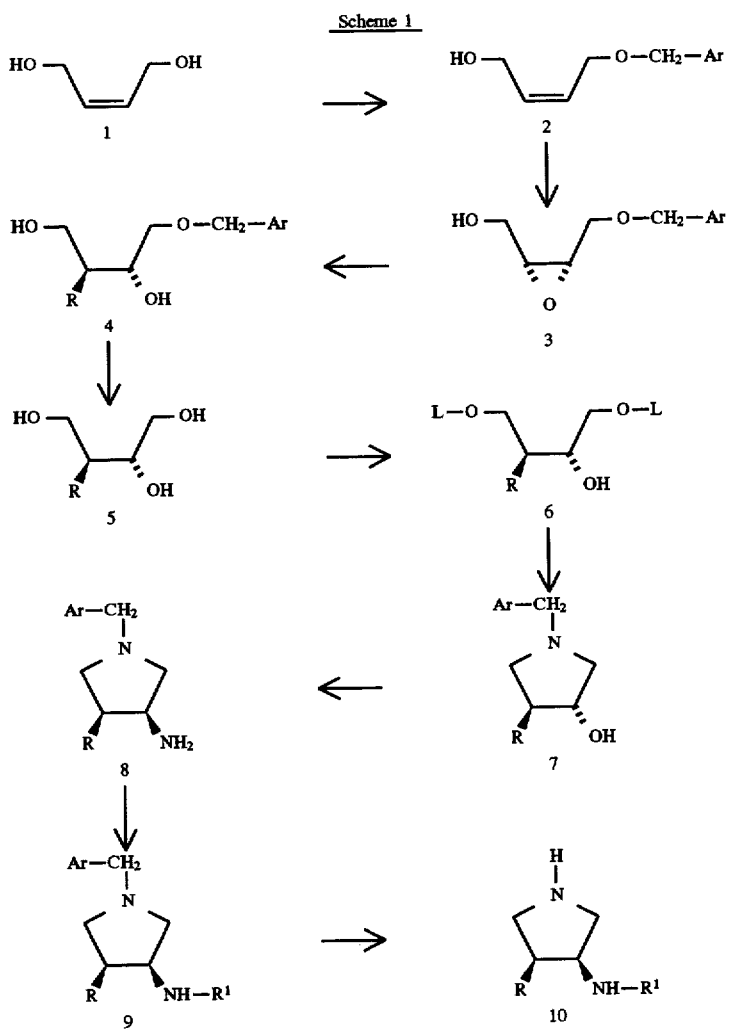

One embodiment of the process of the invention is illustrated in Scheme 1, which describes the manner in which the process may be utilized for preparing the cis-isomers of substituted chiral 3-aminopyrrolidines. A cis-2-butenediol (1) is treated with 1 equivalent of a base, followed by treatment with an arylmethyl halide and a tetraalkylammonium halide to prepare the mono-protected compound (2), wherein Ar represents the aryl moiety. Suitable bases include NaH, $K_2CO_3$, n-butyllithium, lithium bis(trimethylsilylamide), and the like. Illustrative examples of arylmethyl halides include, but are not limited to, benzyl bromide, benzyl chloride, benzyl iodide, 4-bromobenzyl bromide, 4-chlorobenzyl bromide, 4-methoxybenzyl bromide, and the like. The reaction is carried out most easily under an inert atmosphere and anhydrous conditions in an aprotic polar organic solvent, and at a temperature from $-20°$ C. to $25°$ C. for 8 to 24 hours.

Compound (2) is isolated and dried, then chirally oxidized (under the Sharpless Reaction conditions) with titanium isopropoxide, an optically active D-(−)-tartrate ester, for example, D-(−)-diisopropyl tartrate or D-(−)-diethyl tartrate, and tert-butyl hydroperoxide. The reaction is carried out most easily under an inert atmosphere in a suitable anhydrous organic solvent, and also in the presence of 4 Å molecular sieves to remove the water of reaction. Suitable organic solvents include methylene chloride, chloroform, toluene, and the like. The reaction may require stirring at $-20°$ C. to ambient temperature for 0.5 to 48 hours. The reaction is quenched with $Me_2S$ and 10% aqueous tartaric acid solution and stirred at room temperature. The organic layer is separated and washed with water and brine, then dried over $MgSO_4$ to afford the epoxy compound (3).

Compound (3) is then reacted with an R—Mg—X compound, wherein R is $C_1$–$C_6$-alkyl, $C_2$–$C_6$-alkenyl, $C_2$–$C_6$-alkynyl, or $C_3$–$C_6$-cycloalkyl, and X is bromine, chlorine or iodine, under Grignard Reaction conditions, usually in the presence of a copper salt as a catalyst at $-50°$ C. to ambient temperature. Illustrative of, but not limited to, copper salt catalysts are CuCN, CuI, CuCl, or a CuBr—$Me_2S$ complex. The reaction mixture is then preferably treated with $NaIO_4$ or $KIO_4$ to remove 1,2-diol by-products in a polar organic solvent at ambient temperature. Illustrative of, but not limited to, polar organic solvents include tetrahydrofuran, methanol, ethanol, i-propanol, t-butanol, acetone, and the like. The desired compound (4) is separated by chromatography, and the arylmethyl group is then removed to give compound (5). The arylmethyl group may be removed by treatment with sodium in liquid ammonia or by hydrogenolysis in a polar organic solvent at ambient temperature, preferably with the aid of a Pd catalyst, such as Pd/C or palladium acetate.

Compound (5) is then sulfonylated by treatment with a substituted sulfonyl chloride compound to give compound (6), wherein L represents the substituted sulfonyl moiety. Illustrative of, but not limited to, suitable sulfonyl chloride compounds are methanesulfonyl chloride, p-toluenesulfonyl chloride, benzenesulfonyl chloride, and the like.

Compound (6) is then cyclized by treating the chiral diprotected triol compound with an arylmethylamine compound to give compound (7), wherein Ar represents the aryl moiety. This reaction is preferably carried out in a suitable polar organic solvent at an elevated temperature, for example 60° C. to 120° C. Illustrative of, but not limited to, appropriate arylmethylamine compounds are benzylamine, 4-methylbenzylamine, 4-methoxybenzylamine, and the like. The reaction is preferably performed in the presence of base to afford higher yields. Examples of suitable bases for this reaction include, but are not limited to, $NaHCO_3$, $Na_2CO_3$, $KHCO_3$, $K_2CO_3$, triethylamine, pyridine, N-methylmorpholine, N-methylpiperidine, N,N-diisopropylethylamine, and the like.

The hydroxyl group of the chiral pyrrolidine intermediate (7) is then replaced with an amino group by an amination reaction that inverts the chiral center to give compound (8). Suitable replacement reaction conditions include (a) treatment of the hydroxyl group under Mitsunobu Reaction conditions with $Ph_3P$, DEAD, and phthalylamine, followed by treatment with hydrazine; (b) treatment of the hydroxyl group under Mitsunobu Reaction conditions with $Ph_3P$, DEAD, and DPPA followed by reduction of the intermediate azide with $Ph_3P$ and water; (c) reaction of the hydroxyl group with a substituted sulfonyl chloride compound, for example, methanesulfonyl chloride, p-toluenesulfonyl chloride, benzenesulfonyl chloride, followed by replacement of the sulfonyloxy group with an azide group by treatment with sodium or potassium azide and reduction of the intermediate azide with $Ph_3P$ and water.

Compound (8) is then optionally derivatized on the amino group to give compound (9). This may be done by treatment with an amino-protecting group reagent, for example, an acyl chloride, an acyloxy chloride or anhydride, and preferably di-t-butyldicarbonate, trifluoroacetyl chloride or trifluoroacetyl anhydride in an aprotic solvent, or by treatment with an alkyl halide in the presence of base.

Compound (9) is then deprotected by methods known in the art to give the desired compound (10). The arylmethyl group may be removed by treatment with sodium in liquid ammonia or by hydrogenolysis in a polar organic solvent at ambient temperature, preferably with the aid of a Pd catalyst, such as Pd/C or palladium acetate.

Scheme 2

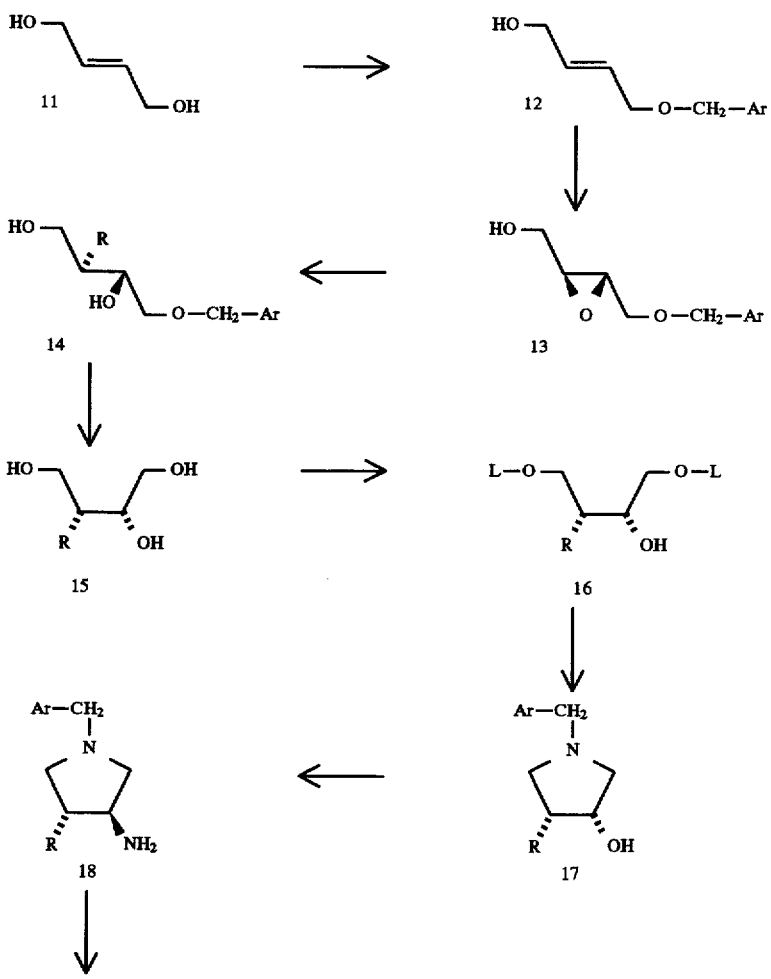

-continued
Scheme 2

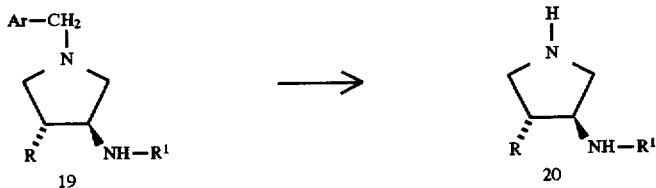

Another embodiment of the process of the invention is illustrated in Scheme 2, which describes the manner in which the process may be utilized for preparing the trans-isomers of substituted chiral 3-aminopyrrolidines. A trans-2-butenediol (11) is treated with 1 equivalent of a base, followed by treatment with an arylmethyl halide and a tetraalkylammonium halide as described in Scheme 1 above to prepare the mono-protected compound (12), wherein Ar represents the aryl moiety. Compound (12) is isolated and dried, then chirally oxidized (under the Sharpless Reaction conditions) with titanium isopropoxide, an optically active L-(+)-tartrate ester, for example, L-(+)-diisopropyl tartrate or L-(+)-diethyl tartrate, and tert-butyl hydroperoxide. Compound (13) is subsequently converted to compound (20) by the same series of reactions as described for the conversion of compound (3) to compound (10) in Scheme 1.

A preferred embodiment of the process of the invention for preparing cis-substituted chiral 3-aminopyrrolidines is that wherein, in step (a) the 2-butene-1,4-diol is the cis isomer; in step (b), the optically active chiral tartrate ester is D-(−)-diisopropyl tartrate; and the product has the cis-3S,4S-configuration.

Another preferred embodiment of the process of the invention for preparing cis-substituted chiral 3-aminopyrrolidines is that wherein, in step (a) the 2-butene-1,4-diol is the cis isomer; in step (b), the optically active chiral tartrate ester is L-(+)-diisopropyl tartrate; and the product has the cis-3R,4R-configuration.

Still another preferred embodiment of the process of the invention for preparing trans-substituted chiral 3-aminopyrrolidines is that wherein in step (a) the 2-butene-1,4-diol is the trans-isomer; in step (b), the optically active chiral tartrate ester is D-(−)-diisopropyl tartrate; and the product has the trans-3R,4S-configuration.

Yet another preferred embodiment of the process of the invention for preparing trans-substituted chiral 3-aminopyrrolidines is that wherein in step (a) the 2-butene-1,4-diol is the trans-isomer; in step (b), the optically active chiral tartrate ester is L-(+)-diisopropyl tartrate; and the product has the trans-3S,4R-configuration.

An additional preferred embodiment of the process of the invention for preparing chiral 3-aminopyrrolidines is that wherein $R^1$ is t-butyloxycarbonyl and in step (a) the 2-butene-1,4-diol is treated with one equivalent of NaH in an aprotic polar organic solvent at from −20° C. to 5° C. under an inert atmosphere and anhydrous conditions, and the arylmethyl halide of the subsequent reaction, performed at ambient temperature for 8 to 24 hours, is selected from the group consisting of benzyl bromide, benzyl chloride, benzyl iodide, 4-bromobenzyl bromide, and 4-chlorobenzyl bromide; in step (b), the first intermediate compound is reacted with titanium isopropoxide, an optically active chiral tartrate ester and tert-butyl hydroperoxide in dry methylene chloride in the presence of 4 Å molecular sieves at −40° C. to −20° C. for 0.5 to 24 hours; in step (c) the Grignard reaction is performed with a CuCN catalyst at −78° to −20° C., followed by treatment of the intermediate with $NaIO_4$ at ambient temperature in aqueous THF; in step (d) the protecting group is removed from the chiral third intermediate compound by hydrogenolysis over Pd/C in an alcoholic solution; in step (e) the fourth intermediate compound (5) is sulfonylated with methanesulfonyl chloride; in step (f) the chiral diprotected triol compound (6) is cyclized with benzylamine in an alcoholic solution and in the presence of a base at 80° C.–120° C.; in step (g) the hydroxyl group of the chiral pyrrolidine intermediate is replaced by treatment with $Ph_3P$, DEAD, and phthalylamine, followed by treatment with hydrazine in ethanol; in step (h), the seventh intermediate compound is derivatized by treatment with di-t-butyldicarbonate; and in step (i), the ring nitrogen of the chiral substituted-aminopyrrolidine compound is deprotected by hydrogenolysis over Pd/C in an alcoholic solution.

A more preferred embodiment of the process of the invention for preparing chiral 3-aminopyrrolidines is that wherein R is $C_{1-C6}$-alkyl.

A specifically preferred embodiment of the process of the invention for preparing chiral 3-aminopyrrolidines is that wherein R is ethyl.

Another aspect of the invention is a process for preparing specific chiral cis- or trans-isomers of the 2,7-diaza-7-substituted-bicyclo[3.3.0]octane, 2,8-diaza-8-substituted-bicyclo[4.3.0]nonane or 2,9-diaza-9-substituted-bicyclo[5.3.0]decane compounds.

Chiral cis-bicyclic compounds may be obtained by the use of the cis-isomer of 2-butene-1,4-diol in step (a) of the process. The chiral cis-bicyclic compound having either the 3S,4S- or the 3R,4R-configuration (analogous to the corresponding 3- and 4-positions of the 3-aminopyrrolidine compounds described in Schemes 1 and 2 above) may be obtained by varying the optically active tartrate ester referred to in step (b) of the process for bicyclic compounds described above. Specifically, when the oxidation is performed with the assistance of the D-(−)-tartrate ester, the 3S,4S-product is obtained. Conversely, when the oxidation is performed with the assistance of the L-(+)-tartrate ester, the 3R,4R-product is obtained.

Chiral trans-bicyclic compounds may be obtained by the use of the trans-isomer of 2-butene-1,4-diol in step (a) of the process. The chiral trans-bicyclic compound having either the 3S,4R- or the 3R,4S-configuration (analogous to the corresponding 3- and 4-positions of the 3-aminopyrrolidine compounds described in Schemes 1 and 2 above) may be obtained by varying the optically active tartrate ester referred to in step (b) of the trans-process described above. Specifically, when the oxidation is performed with the assistance of the L-(+)-tartrate ester, the 3S,4R-product is obtained. Conversely, when the oxidation is performed with the assistance of the D-(−)-tartrate ester, the 3R,4S-product is obtained.

The process of the invention for obtaining specific chiral cis- and trans-isomers of the desired bicyclic compounds may be better understood by reference to the reaction Schemes 3 and 4 illustrated below.

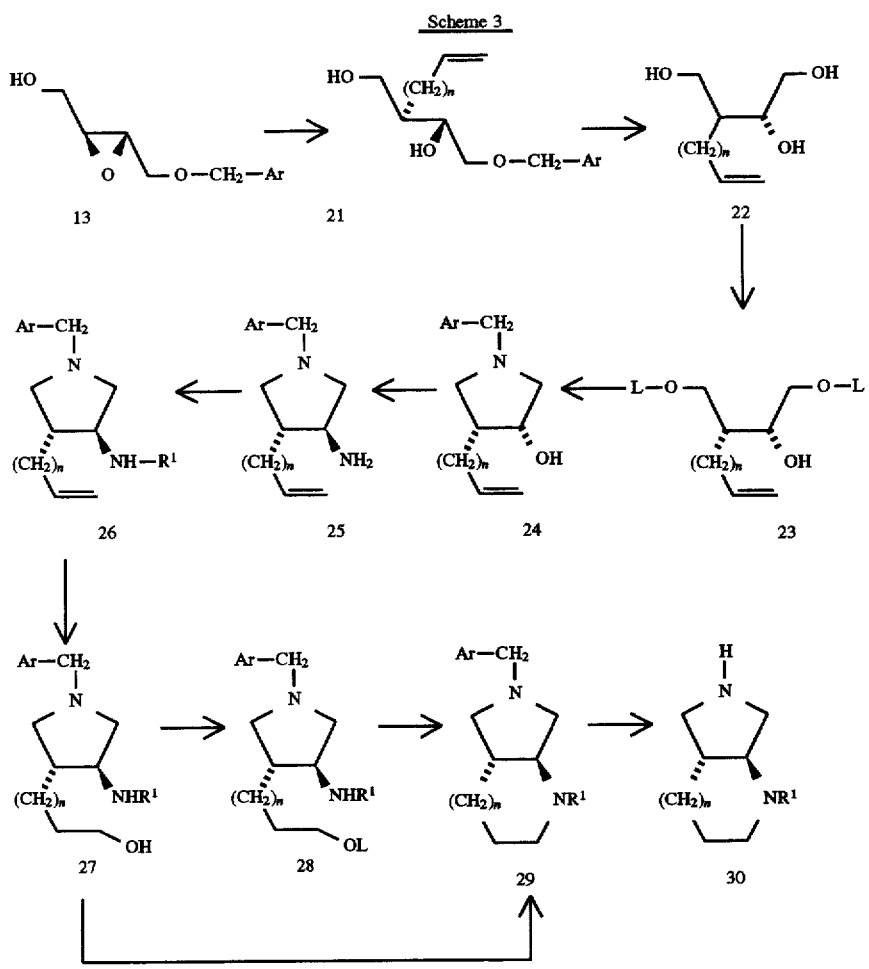

Scheme 3 describes the manner in which the process may be utilized for preparing the trans-isomers of chiral 2,7-diaza-7-substituted-bicyclo[3.3.0]octane, 2,8-diaza-8-substituted-bicyclo[4.3.0]nonane and 2,9-diaza-9-substituted-bicyclo[5.3.0]decane compounds. Compound (13) (prepared from trans-2-butene-1,4-diol as shown in Scheme 2) is reacted with a vinyl, allyl or 3-butenylmagnesium halide, wherein the halide is bromine, chlorine or iodine, under Grignard Reaction conditions, as described in Scheme 1 to give compound (21). The reaction mixture is then preferably treated with $NaIO_4$ or $KIO_4$ to remove 1,2-diol by-products in a polar organic solvent at ambient temperature. Compound (21) is subsequently converted to compound (26) by the same series of reactions as described for the conversion of compound (3) to compound (9) in Scheme 1.

Compound (26) is then oxidized with a hydroboration reagent, for example $BH_3$ in the presence of hydroxide ion and $H_2O_2$, to give compound (27).

Compound (27) is treated with a substituted sulfonyl chloride compound to give compound (28), wherein L represents the substituted sulfonyl moiety.

Compound (28) is then cyclized to compound (29) by treatment with NaH under anhydrous conditions in an aprotic solvent.

Alternately, compound (27) may be directly converted into compound (29) by treatment under Mitsunobu Reaction conditions with $Ph_3P$ and DEAD in an aprotic solvent.

Compound (29) is then deprotected to give the desired compound (30). The arylmethyl group may be removed by treatment with sodium in liquid ammonia or by hydrogenolysis in a polar organic solvent at ambient temperature, preferably with the aid of a Pd catalyst, such as Pd/C or palladium acetate.

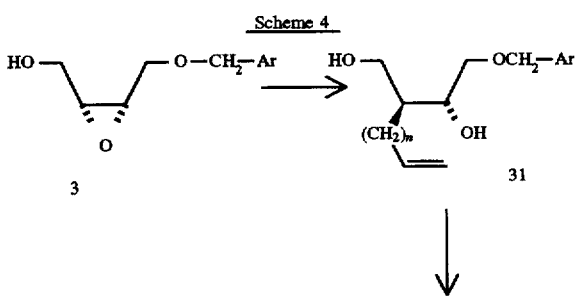

-continued
Scheme 4

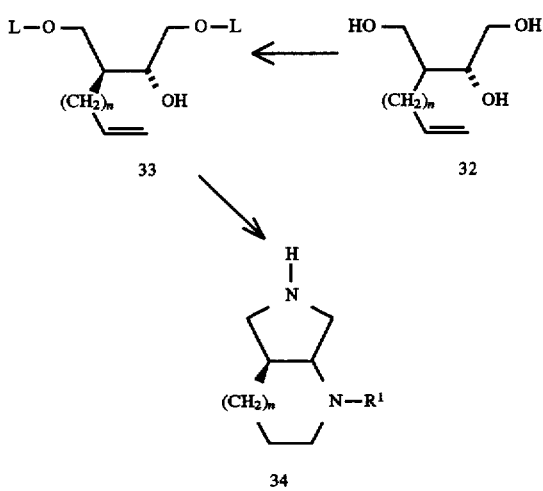

Scheme 4 describes the manner in which the process may be utilized for preparing the cis-isomers of chiral 2,7-diaza-7-substituted-bicyclo[3.3.0]octane, 2,8-diaza-8-substituted-bicyclo[4.3.0]nonane and 2,9-diaza-9-substituted-bicyclo[5.3.0]decane compounds. Compound (3) (prepared from cis-2-butene-1,4-diol as shown in Scheme 1) is reacted with a vinyl, allyl or 3-butenylmagnesium halide, wherein the halide may be bromine, chlorine or iodine, under Grignard Reaction conditions as described in Scheme 1 to give compound (31). The reaction mixture is then preferably treated with $NaIO_4$ or $KIO_4$ to remove 1,2-diol by-products in a polar organic solvent at ambient temperature.

Compound (31) is subsequently converted to compound (33) by the same series of reactions as described for the conversion of compound (21) to compound (30) in Scheme 3.

One embodiment of the process described in Schemes 3 and 4 is that in which steps (j) and (k) are combined into one step, in which the compound having the formula

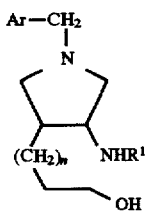

is treated with triphenylphosphine and diethylazodicarboxylate under Mitsunobu Reaction conditions, and isolating the chiral bicyclic compound having the formula:

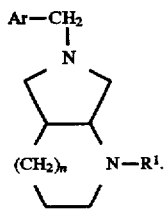

A preferred embodiment of the process of the invention is that for preparing cis-isomers of chiral 2,7-diaza-7-substituted-bicyclo[3.3.0]octane, 2,8-diaza-8-substituted-bicyclo[4.3.0]nonane and 2,9-diaza-9-substituted-bicyclo[5.3.0]decane compounds wherein, in step (a) the 2-butene-1,4-diol is the cis isomer, in step (b), the optically active chiral tartrate ester is D-(−)-diisopropyl tartrate, and the product has the S,S-configuration at the chiral centers.

Another preferred embodiment of the process of the invention is that for preparing cis-isomers of chiral 2,7-diaza-7-substituted-bicyclo[3.3.0]octane, 2,8-diaza-8-substituted-bicyclo[4.3.0]nonane and 2,9-diaza-9-substituted-bicyclo[5.3.0]-decane compounds wherein, in step (a) the 2-butene-1,4-diol is the cis-isomer, in step (b), the optically active chiral tartrate ester is L-(+)-diisopropyl tartrate, and the product has the R,R-configuration at the chiral centers.

Stir another preferred embodiment of the process of the invention is that for preparing trans-isomers of chiral 2,7-diaza-7-substituted-bicyclo[3.3.0]octane, 2,8-diaza-8-substituted-bicyclo[4.3.0]nonane and 2,9-diaza-9-substituted-bicyclo[5.3.0]-decane compounds wherein, in step (a) the 2-butene-1,4-diol is the trans-isomer, in step (b), the optically active chiral tartrate ester is D-(−)-diisopropyl tartrate; and the product has the R,S-configuration at the chiral centers.

Yet another preferred embodiment of the process of the invention is that for preparing trans-isomers of chiral 2,7-diaza-7-substituted-bicyclo[3.3.0]octane, 2,8-diaza-8-substituted-bicyclo[4.3.0]nonane and 2,9-diaza-9-substituted-bicyclo[5.3.0]-decane compounds wherein, in step (a) the 2-butene-1,4-diol is the trans-isomer, in step (b), the optically active chiral tartrate ester is L-(+)-diisopropyl tartrate; and the product has the S,R-configuration at the chiral centers.

An additional preferred embodiment of the process of the invention for preparing chiral 2,7-diaza-7-substituted-bicyclo[3.3.0]octane, 2,8-diaza-8-substituted-bicyclo[4.3.0]nonane and 2,9-diaza-9-substituted-bicyclo[5.3.0]decane compounds is that wherein $R^1$ is t-butyloxycarbonyl and in step (a) the 2-butene-1,4-diol is treated with one equivalent of NaH in an aprotic polar organic solvent at from −20° C. to 5° C. under an inert atmosphere and anhydrous conditions, and the arylmethyl halide of the subsequent reaction, performed at ambient temperature for 8 to 24 hours, is selected from the group consisting of benzyl bromide, benzyl chloride, benzyl iodide, 4-bromobenzyl bromide, and 4-chlorobenzyl bromide; in step (b), the first intermediate compound is reacted with titanium isopropoxide, an optically active chiral tartrate ester and tert-butyl hydroperoxide in dry methylene chloride in the presence of 4 Å molecular sieves at −40° C. to −20° C. for 0.5 to 24 hours; in step (c) the Grignard reaction is performed with a CuCN catalyst at −78° to −20° C., followed by treatment of the intermediate with $NaIO_4$ at ambient temperature in aqueous THF; in step (d) the protecting group is removed from the chiral third intermediate compound by treatment with Na and $NH_3$; in step (e) the fourth intermediate compound (5) is sulfonylated with methanesulfonyl chloride; in step (f) the chiral diprotected triol compound (6) is cyclized with benzylamine in an alcoholic solution and in the presence of a base at 80° C.–120° C.; in step (g) the hydroxyl group of the chiral pyrrolidine intermediate is replaced by treatment with $Ph_3P$, DEAD, and phthalylamine, followed by reaction with hydrazine in ethanol; in step (h), derivatizing the amino group by treatment with di-t-butyldicarbonate; in step (i) the hydroborating reagent is $BH_3$ in the presence of hydroxide ion and $H_2O_2$; in step (j) the substituted sulfonyl chloride is methanesulfonyl chloride; in step (k) cyclizing by treatment with NaH under anhydrous conditions in an aprotic solvent; and in step (l)

deprotecting the ring nitrogen by hydrogenolysis over Pd/C in an alcoholic solution.

A more preferred embodiment of the process of the invention for preparing chiral 2,7-diaza-7-substituted-bicyclo[3.3.0]octane, 2,8-diaza-8-substituted-bicyclo[4.3.0] nonane and 2,9-diaza-9-substituted-bicyclo[5.3.0]decane compounds is that wherein $R^1$ is $C_1$–$C_6$-alkyl.

A specifically preferred embodiment of the process of the invention for preparing chiral 2,7-diaza-7-substituted-bicyclo[3.3.0]octane, 2,8-diaza-8-substituted-bicyclo[4.3.0] nonane and 2,9-diaza-9-substituted-bicyclo[5.3.0]decane compounds is that wherein $R^1$ is hydrogen or methyl.

EXAMPLES

The invention may be better understood by reference to the following examples, which are provided for the illustration and not limitation of the invention.

EXAMPLE 1

Reference synthesis of 1-cyclopropyl-8-(S,S-2,8-diaza-8-bicyclo[4.3.0]-nonyl)-7-fluoro-4H-9-methyl-4-oxo-quinolizine-3-carboxylic acid hydrochloride Step 1a. 6-(1-(S)-phenylethyl))-5,7-dihydro-6H-pyrrolo [3,4-b]pyridine-5,7-dione A 10 g sample of 2,3-pyridinedicarboxylic anhydride (Aldrich) was dissolved in 100 mL of anhydrous THF and cooled to 0° C. To this solution was added 8.70 mL of (S)-(−)-alpha-methylbenzylamine. The solution was warmed to room temperature and stirred for 30 minutes, then 11.96 g of 1,1'-carbonyldiimidazole was added. The reaction was stirred at room temperature under $N_2$ for 20 hours. The solvent was removed, and the residue was dissolved in methylene chloride. The solvent was washed with water and dried over $MgSO_4$. The solvent was removed under vacuum to give 15.344 g of the title compound.

Step 1b. 8-(1-(S)-phenylethyl)-2,8-diazobicyclo[4.3.0] nonan-7,9-dione

A 15.344 g sample of the compound from step 1a above was hydrogenated over Pd/C in 2-methoxyethanol at 4 atm $H_2$ and 100° C. for 22 hours. The catalyst and solvent were removed to give 10.12 g of the title compound. Step 1c. 8-(1-(S)-phenylethyl)-2,8-diazobicyclo[4.3.0]nonane A 10.12 g sample of the compound from step 1b was dissolved in 30 mL of THF, and this solution was added dropwise to a suspension of 3.13 g of LAH in 50 mL of anhydrous THF stirred at 0° C. under $N_2$. After addition was complete, the mixture was heated at reflux for 9 hours. The reaction was quenched at 0° C. by sequential addition of 25 mL of $H_2O$, 25 mL of 15% KOH and 25 mL of $H_2O$. The solids were removed by filtration, and the filtrate was extracted with ether. The extract was dried over $MgSO_4$, and the solvent was removed to give 7.98 g of the title compound.

Step 1d. 2-BOC-8-(1-(S)-phenylethyl)-2,8-diazobicyclo [4.3.0]nonane

A 7.98 g sample of the compound from step 1c above was dissolved in 75 mL of 2:1 methanol:$H_2O$. The solution was cooled to 0° C., and 7.94 g of di-t-butyl dicarbonate was added. The mixture was then warmed to room temperature and stirred for 1 hour. The organic solvent was removed under vacuum, and the residue was slurried with methylene chloride. The organic phase was separated, washed and dried. The solvent was removed, and the residue was purified by chromatography on silica gel, eluting with 100:5:0.5 methylene chloride:methanol:ammonium hydroxide, to give 4.6 g of the title compound as an oil. This material was separated into the 1,6-(R,R)- and 1,6-(S,S)-isomers by HPLC using a chiral support. The R,R-isomer had an $[\alpha]_D$ of +31.9° C. (23°, c=1.01, methanol); The S,S-isomer had an $[\alpha]_D$ of −84.6° C. (23°, c=1.04, methanol) (for additional information on assignment of isomers, refer to Poster #642, ICAAC 32nd Annual Meeting, 1994).

Step 1e. (S,S)-2-BOC-2,8-diazobicyclo[4.3.0]nonane

A 1.328 g sample of the S,S-isomer from step 1d above and 1.27 g of ammonium formate were dissolved in 40 mL of methanol. The flask was flushed with $N_2$, 130 mg of 10% Pd/C was added, and the reaction mixture was heated at reflux for 1.5 hours. The solution was cooled and filtered, then the solvent was removed. The residue was dissolved in methylene chloride and filtered again. The solvent was removed under vacuum to give the title compound (858 mg). $[\alpha]_D$−70.8° C. (23°, c=1.30, methanol).

Step 1f. 1-cyclopropyl-8-(S,S-2,8-diaza-8-bicyclo[4.3.0] nonyl)-7-fluoro-4H-9-methyl-4-oxo-quinolizine-3-carboxylic acid hydrochloride A sample of 1-cyclopropyl-8-chloro-7-fluoro-4H-9-methyl-4-oxo-quinolizine-3-carboxylic acid ethyl ester was dissolved in anhydrous acetonitrile, and sodium bicarbonate and 1,6-(S,S)-2-BOC-2,8-diazobicyclo[4.3.0]nonane (from step 1e above) were added. The mixture was heated at reflux under nitrogen for 7 hours, then the solvent was removed and the residue was redissolved in methylene chloride. This solution was washed with water, 5% HCl, water, and concentrated. The residue was purified by flash chromatography, eluting with 100:10 methylene chloride:methanol, followed by 100:10:0.5 methylene chloride:methanol:$NH_4OH$. Removal of the solvent gave the free base of the ester of the title compound. The ester was hydrolyzed by treatment with LiOH.$H_2O$ in aqueous THF under nitrogen for 3 hours. The THF was removed under vacuum, and the residue was adjusted to a pH between 2 and 4 with 1 N HCl. The solid was collected, and the filtrate was extracted with methylene chloride and washed and concentrated to give additional product. The combined solids were purified by flash chromatography eluting with 100:5:1 methylene chloride:methanol:acetic acid to yield free base of the title compound. The base was converted to the HCl salt by treatment with HCl in ether/methylene chloride. The precipitate was collected by filtration and washed with ether. The solid was dissolved in water, filtered through a sintered glass funnel, and freeze-dried to give the title product. mp 230°–232° C. (dec). MS 346 (M—Cl )$^+$; $^1$H NMR (DMSO) δ: 0.58 (m, 2H), 0.99 (m, 2H), 2.15 (m, 1H), 2.31 (m, 2H), 2.63 (s, 3H), 3.77 (m, 2H), 3.99–4.06 (m, 3H), 7.94 (s, 1H), 8.39 (br s, 3H), 9.10 (d, 1H, J+11 Hz), 13.85 (br s); IR 3440, 1695, 1610 cm$^{-1}$.

EXAMPLE 2

Reference synthesis of 8-(trans-3-amino-4-ethylpyrrolidin-1-yl)-1-cyclopropyl-7-fluoro-4H-9-methyl-4-oxo-quinolizine-3-carboxylic acid hydrochloride diastereomer A Step 2a. 2-pentenoic acid ethyl ester Propionaldehyde (5.8 g) and (carbethoxymethylene)triphenylphosphorane (35 g) were dissolved in methylene chloride (100 mL), and the mixture was refluxed overnight. The product was distilled off from the reaction mixture.

Step 2b. trans-3-(BOC-amino)-1-CBZ-4-ethyl-pyrrolidine

The compound from step 2a and 5 g of N-benzyl-N-(methoxymethyl)trimethyl-silylamine were dissolved in 30 mL of dry methylene chloride. The solution was stirred at 0° C., and 1% trifluoroacetic acid was added dropwise. The mixture was then stirred for 1.5 hours at room temperature. The solvent was removed, and the residue was chromatographed on silica gel to give the title compound.

Step 2c. trans-1-CBZ-3-(BOC-amino)-4-ethylpyrrolidine

The compound from step 2b was dissolved in 20 mL of ethanol, and 10 equivalents of ammonium formate and 170 mg of 10% Pd/C were added. The reaction mixture was heated at reflux and stirred for 30 minutes. The mixture was filtered, and the filtrate was evaporated. The residue was dissolved in 10 mL of dioxane and 2.5 mL of water, and 20% $Na_2CO_3$ was added. The mixture was cooled to 0° C., and 1.5 equivalents of benzyloxy-carbonyl chloride was added slowly. The reaction was stirred for 30 minutes, then diluted with 100 mL of ether. The organic layer was separated, washed with brine and dried over $MgSO_4$. The solvent was removed, and the residue was chromatographed on silica gel. This product was dissolved in 12 mL of THF, the solution was cooled to 0° C., and 4 equivalents of LiOH in 3 mL of water were added. The mixture was stirred at 0° C. for 2 hours, then diluted with water and acidified with 2 N HCl to pH 2. The mixture was extracted with ether, and the extract was washed with brine and dried. The solvent was removed, and the residue was chromatographed on silica gel to give the intermediate acid. This compound was dissolved in 10 mL of anhydrous t-butanol, and 1.1 equivalent of DPPA and 4 equivalents of triethylamine were added. The mixture was heated at reflux for 24 hours, then cooled. The solvent was removed, and the residue was chromatographed on silica gel. The diastereomers were separated by chiral HPLC on a Chiralpak AS™ column, and diastereomer A (chirality not determined) was carried forward to the next step. $^1$H NMR (CDCl$_3$) δ: 7.4 (m, 5H), 5.18 (s, 2H), 6.4–4.60 (m, 3H), 4.30 (m, 1H), 3.60–3.80 (m, 3H), 3.10 (m, 2H), 1.95 (m, 1H), 1.60 (m, 1H), 1.30 (m, 1H), 0.95 (t, 3H), 1.95 (s, 9H). Diastereomer B (chirality not determined) was carried forward to Example 573.

Step 2d. trans-3-(BOC-amino)-4-ethyl-pyrrolidine

The compound from step 2c was hydrogenated with Pd/C in ethanol, and the title compound was isolated.

Step 2e. 8-(trans-3-amino-4-ethylpyrrolidin-1-yl)-1-cyclopropyl-7-fluoro-4H-9-methyl-4-oxo-quinolizine-3-carboxylic acid hydrochloride A sample of 1-cyclopropyl-8-chloro-7-fluoro-4H-9-methyl-4-oxo-quinolizine-3-carboxylic acid ethyl ester was dissolved in anhydrous acetonitrile, and sodium bicarbonate and trans-3-(BOC-amino)-4-ethyl-pyrrolidine (from step 2d above) were added. The mixture was heated at reflux under nitrogen for 7 hours, then the solvent was removed and the residue was redissolved in methylene chloride. This solution was washed with water, 5% HCl, water, and concentrated. The residue was purified by flash chromatography, eluting with 100:10 methylene chloride:methanol. Removal of the solvent gave the free base of the ester of the title compound. The ester was hydrolyzed by treatment with LiOH.H$_2$O in aqueous THF under nitrogen for 3 hours. The THF was removed under vacuum, and the residue was adjusted to a pH between 2 and 4 with 1 N HCl. The solid was collected, and the filtrate was extracted with methylene chloride and washed and concentrated to give additional product. The combined solids were purified by flash chromatography eluting with 100:5:1 methylene chloride:methanol:acetic acid to yield the free base of the title compound. The base was converted to the HCl salt by treatment with HCl in ether/methylene chloride. The precipitate was collected by filtration and washed with ether. The solid was dissolved in water, filtered through a sintered glass funnel, and freeze-dried to give the title product. MS m/z 474 (M+H)$^+$. $^1$H NMR (DMSO-d$_6$) & 9.10 (d, 1H), 8.50 (s, 1H), 4.10 (m, 2H), 3.50–3.80 (m, 3H), 2.60 (s, 3H), 2.30 (m, 2H), 1.7 (m, 1H), 1.40 (m, 1H), 1.0 (m, 5H), 0.6 (m, 2H).

EXAMPLE 3

Reference synthesis of 8-(cis-3-amino-4-ethylpyrrolidin-1-yl)-1-cyclopropyl-7-fluoro-4H-9-methyl-4-oxo-quinolizine-3-carboxylic acid hydrochloride diastereomer A Step 3a. 1-CBZ-3-pyrroline 3-Pyrroline (Aldrich, 65% purity) was dissolved in a 1:1 mixture of dioxane and H$_2$O.Na$_2$CO$_3$ was added. The reaction mixture was then flushed with N$_2$ and cooled to 0° C. Benzylchloroformate was added dropwise and the mixture was stirred at 0° C. for several hours. The reaction mixture was allowed to reach room temperature and was stirred for an additional 2 hours. Ethyl acetate was then added and the reaction mixture was washed with H$_2$O and brine. The organic layer was dried over MgSO$_4$, concentrated in vacuo and column chromatographed in a hexane/EtOAc solution to afford the title compound (65% purity).

Step 3b. 3,4-epoxy-1-CBZ-pyrroline

Five grams of crude 1-CBZ-3-pyrroline from step 3a was dissolved in 25 mL of CH$_2$Cl$_2$. 3-Chloroperoxybenzoic acid was added over 5 minutes, and the reaction mixture was allowed to stir at room temperature for 22 hours. The reaction mixture was then filtered, and filtrate was diluted with 30 mL of CH$_2$Cl$_2$ and washed with Na$_2$S$_2$O$_3$ solution, NaHCO$_3$ solution and H$_2$O. The organic layer was dried over MgSO$_4$, concentrated in vacuo, and chromatographed on silica gel eluting with hexane/EtOAc solution. The title compound was obtained in 76% yield. MS m/z 220 (M+H)$^+$. $^1$H NMR (CDCl$_3$)δ: 3.35 (ddd, 2H), 3.65–3.70 (m, 2H), 3.80–3.90 (dd, 2H), 5.15 (d, 2H), 7.30–7.40 (m, 5H).

Step 3c. cis-3-(hydroxy)-1-CBZ-4-ethyl-pyrrolidine

The compound from step 3b (2.0 g) was dissolved in 20 mL of THF, and CuCN (0.081 g) was added. The mixture was cooled to −70° C., and 5.5 mL of EtMgCl solution was then added over 20 minutes. The mixture was allowed to warm to −50° C. and was stirred at this temperature for 1 hour. The solution was then allowed to warm to −20° C. over the next hour. Finally, the solution was left to stir overnight and allowed to reach room temperature. The following morning, the reaction was quenched with 2N HCl. EtOAc was added, and the layers were separated. The organic layer was washed with H$_2$O and saturated NaCl solution, dried over MgSO$_4$, concentrated in vacuo, and chromatographed on silica gel to give the title compound in 88% yield. MS m/z 250 (M+H)$^+$. $^1$H NMR (CDCl$_3$) δ: 0.90–1.00 (t, 3H), 1.15–1.35 (m, 1H), 1.45–1.65 (m, 3H), 1.90–2.05 (m, 1H), 3.10–3.25 (m, 1H), 3.25–3.40 (m, 1H), 3.60–3.75 (m, 2H), 5.14 (s, 2H), 7.25–7.40 (m, 5H). p Step 3d. cis-3-(phthalimide)-1-CBZ-4-ethyl-pyrrolidine The compound from step 3c (5.22 g), PPh$_3$ (8.24 g) and phthalimide (4.0 g) were placed in a flask, flushed with N$_2$, cooled to 0° C., and dissolved in 50 mL of THF. DEAD (4.3 mL) was then added dropwise over 25 minutes. The resultant solution was stirred for 51 hours at room temperature. The solvent was then removed in vacuo and the product was purified by column chromatography to give the title compound in 86% yield. MS m/z 379 (M+H)$^+$. $^1$H NMR (CDCl$_3$) δ:0.85–0.95 (m, 2H), 1.15–1.40 (m, 3H), 2.37–2.53 (m, 1H), 3.42 (t, 1H), 3.75–4.00 (m, 2H), 4.10–4.35 (m, 1H), 7.27–7.45 (m, 5H), 7.72–7.80 (m, 2H), 7.80–7.90 (m, 2H).

Step 3e. cis-3-(BOC-amino)-1-CBZ-4-ethyl-pyrrolidine

The compound from step 3d (6.56 g) was dissolved in EtOH, $NH_2NH_2.H_2O$ (2.7 mL) was added and the mixture was refluxed for 5.5 hours. The reaction mixture was then cooled, filtered, and the filtrate was concentrated in vacuo. The residue was dissolved in 20 mL of $CH_2Cl_2$ and cooled to 0° C. $BOC_2O$ (4.9 g), $Et_3N$ (3.0 mL), and a catalytic amount of DMAP were added and the mixture was allowed to reach room temperature while stirring overnight. The following morning $CH_2Cl_2$ was added, and the mixture was washed with $NaHCO_3$ solution, $H_2O$ and brine. The organic layer was dried over $MgSO_4$, concentrated in vacuo and column chromatographed in a hexane/EtOAc solution. The diastereomers were separated by chiral HPLC on a Chiralpak AS™ column. Diastereomer A was carried forward to the next step. MS m/z 349 (M+H)$^+$.$^1$H NMR ($CDCl_3$) δ:0.90–1.00 (td, 3H), 1.20–1.50 (m, 2H), 1.45 (s, 9H), 2.05–2.12 (m, 1H), 3.01 (q, 1H), 3.41 (t, 1H), 3.51–3.71 (m, 2H), 4.24 (broad s, 1H), 4.53 (broad s, 1H), 5.13 (s, 2H), 7.18–7.40 (m, 5H). Diastereomer B was carried forward to Example 575.

Step 3f. cis-3-(BOC-amino)-4-ethyl-pyrrolidine

The compound from step 3e was hydrogenated with Pd/C in ethanol as in Example 2d, and the title compound was isolated. MS m/z 215 (M+H)$^+$.$^1$H NMR ($CDCl_3$)δ: 0.90–1.00 (m, 3H), 1.42 (s, 9H), 2.00–2.10 (m, 2H), 2.50–2.60 (m, 1H), 2.80–2.90 (m, 1H), 3.15–3.25 (m, 2H), 4.12–4.25 (m, 1H), 4.75–4.85 (m, 1H).

Step 3g. 8-(cis-3-amino-4-ethylpyrrolidin-1-yl)-1-cyclopropyl-7-fluoro-4H-9-methyl-4-oxo-quinolizine-3-carboxylic acid hydrochloride A sample of 1-cyclopropyl-8-chloro-7-fluoro-4H-9-methyl-4-oxo-quinolizine-3-carboxylic acid ethyl ester was dissolved in anhydrous acetonitrile, and sodium bicarbonate and cis-3-(BOC-amino)-4-ethyl-pyrrolidine (from step 3f above) were added. The mixture was heated at reflux under nitrogen for 7 hours, then the solvent was removed and the residue was redissolved in methylene chloride. This solution was washed sequentially with water, 5% HCl and water again. The organic layer was concentrated, and the residue was purified by flash chromatography, eluting with 100:10 methylene chloride:methanol. Removal of the solvent gave the free base of the ester of the title compound. The ester was hydrolyzed by treatment with $LiOH.H_2O$ in aqueous THF under nitrogen for 3 hours. The THF was removed under vacuum, and the residue was adjusted to a pH between 2 and 4 with 1 N HCl. The solid was collected, and the filtrate was extracted with methylene chloride and washed and concentrated to give additional product. The combined solids were purified by flash chromatography eluting with 100:5:1 methylene chloride:methanol:acetic acid to yield the free base of the title compound. The base was convened to the HCl salt by treatment with HCl in ether/methylene chloride. The precipitate was collected by filtration and washed with ether. The solid was dissolved in water, filtered through a sintered glass funnel, and freeze-dried to give the title product. MS m/z 374 (M+H)$^+$.$^1$H NMR (DMSO-$d_6$)δ: 13.80 (broad s, 1H), 9.14 (d, 1H), 8.42 (s, 2H), 7.78 (s, 1H), 4.20–4.30 (m, 1H), 3.85–3.95 (m, 2H), 3.78 (d, 1H), 3.66 (t, 1H), 2.61 (s, 3H), 2.33–2.5 (m, 1H), 2.20–2.32 (m, 1H), 1.39–1.61(m, 2H), 0.82–1.10 (m, 5H), 0.48–0.53 (m, 2H).

EXAMPLE 4

(3S ,4S )-3-BOC-amino-4-ethyl-pyrrolidine

Step 4a. (Z)-4-[(4-bromobenzyl)oxy]-2-buten-1-ol

To a cold (0° C.) stirred suspension of NaH (4.8 g, 0.12 mol of a 60% dispersion in oil previously washed with 3×70 mL of dry hexane ) in dry THF (400 mL) under an atmosphere of nitrogen was added cis-2-butene-1,4-diol (49 mL, 53 g, 0.6 mol) over 10 minutes. The ice bath was removed and the resulting tan solution was stirred at room temperature for 30 minutes. Tetrabutylammonium iodide (300 mg) and 4-bromobenzyl bromide (25 g) were then added, and the resulting reaction mixture was stirred at room temperature overnight. Water (5 mL) was added, and the THF was removed by rotary evaporation. The residue was taken up in $Et_2O$ (250 mL), washed with 5×100 mL water and dried ($MgSO_4$). Concentration and Kugelrohr distillation afforded the monoprotected diol as a light yellow oil (22 g, 92%).

Step 4b. (2R,3S)-3-[[(4-bromobenzyl)oxy]methyl]oxirane-2-methanol

To a cold (−25° C.) stirred suspension of powdered 4 Å molecular sieves (13.5 g) in dry $CH_2Cl_2$ (800 mL) under an atmosphere of nitrogen was added titanium isopropoxide (9.95 g), D-(−)-diisopropyl tartrate (11.2 g ) and tert-butyl hydroperoxide (63.6 mL of a 5–6M solution in decane). The slurry was stirred at −25° C. for 30 minutes. Allylic alcohol (45 g) was then added as a solution in $CH_2Cl_2$ (200 mL), the resulting mixture was stirred at −25° C. for 2 hours and stored at −20° C. freezer for 2 days, and 2 mL of $Me_2S$ and 200 mL of a 10% aqueous tartaric acid solution were added. The solution was stirred for 30 minutes, then allowed to warm to room temperature. It was stirred for an additional 2 hours at room temperature, and the organic layer was separated, washed with water and brine, and dried over $MgSO_4$. The solvent was removed, and the residue was dissolved in 300 mL of ether and 200 mL of pentane. The solution was slowly cooled to −20° C. and left overnight. The white needles were collected by filtration, washed with pentane and dried in vacuo to afford the title compound (30 g).

Step 4c. (2S,3R)-2-ethyl-4-bromobenzyloxy-1-butan-1,3-diol

To a stirred suspension of CuCN (2.68 g, 30 mmol) in 1000 mL dry $Et_2O$ under nitrogen at −50° C. was added 300 mL of ethyl magnesium bromide (2.0M in ether). The resulting suspension was stirred for 30 minutes, then 27.3 g of the epoxy alcohol from step 4b in 150 mL THF was added slowly via cannula. The reaction mixture was stirred at −50° C. for 5 hours and at −30° C. for an additional 2 hours. The temperature was then allowed to reach 0° C. over 2 hours. Aqueous solutions of $NH_4OH$ and $NH_4Cl$ were added, and the mixture was extracted with ether. The organic extract was washed with saturated NaCl, dried over $MgSO_4$, and filtered, and the solvent was evaporated to afford 31.2 g of a heavy oil. The oil was dissolved in 300 mL of a 2:1 mixture of $THF—H_2O$. $NaIO_4$ (14.2 g) was added to the solution, and the mixture was stirred at room temperature for 4 hours. The THF was removed by rotary evaporation. Ethyl acetate and brine were then added, the layers were separated, and the organic layer was dried over $MgSO_4$, filtered, concentrated, and column chromatographed to afford 20.93 g of the title compound.

Step 4d. (2R,3S)-2-ethylbutan-1,3,4-triol

The compound prepared from step 4c was subjected to hydrogenation under 1 atm of $H_2$ for 24 hours at room temperature in 500 mL of EtOH containing 2 eq NaHCO₃ and 10% Pd/C as catalyst. After filtration, the solvent was removed, and the residue was taken up in ethyl acetate and methylene chloride (1:1) solution. The solution was filtered, and the filtrate was evaporated to afford the desired product (86% yield).

Step 4e. (3R,4S)-1-benzyl-4-ethyl-pyrrolidin-3-ol

To a solution of 4.6 g of the product from step 4d in 60 mL pyridine cooled to −40° C., MsCl (7.85 g) was added slowly via syringe. The mixture was stirred for 4 hours at −40° C. Water (10 mL) was added, and the reaction mixture was allowed to warm to room temperature. The solvent was removed, and the residue was taken up in ethyl acetate. The solvent was washed with water, 2 M HCl, NaHCO₃ and brine, and dried over MgSO₄. The solution was filtered and concentrated to afford the desired dimesylate compound (85% yield). The dimesylate compound (16.27 g) was dissolved in 300 mL of absolute EtOH, and 28.22 g NaHCO₃ and 7.21 g of benzyl amine were added. The mixture was heated to reflux under N₂ for 16 hours, then allowed to cool to room temperature. The solvent was removed under vacuum, 500 mL ethyl acetate and 200 mL water were added, and the layers were separated. The organic layer was washed with brine, dried over MgSO₄, filtered, and concentrated to afford 10.6 g of the desired product.

Step 4f. (3S,4S)-1-benzyl-3-BOC-amino-4-ethyl-pyrrolidine

To a solution of 4.24 g of the compound from step 4e in 50 mL THF were added 5.90 g triphenyl phosphine and 3.31 g phthalimide, then DEAD (3.91 g) was added via syringe. The resulting solution was stirred for 1 hour at room temperature then concentrated to dryness. The residue was dissolved in 50 mL of absolute ethanol, 1.22 g hydrazine monohydrate was added, and the mixture was refluxed under N₂ for 4 hours. After cooling to room temperature, concentrated HCl (5.5 mL) was added, the solid was filtered, and filtrate was concentrated. Water and CH₂Cl₂ (100 mL of each) were added to the residue. The water layer was separated and extracted twice with CH₂Cl₂, then basified with 20% NaOH. The aqueous solution was extracted with CH₂Cl₂. The organic layer was concentrated and redissolved in 50 mL of a 1:1 mixture of methanol-water, then 4.91 g of di-t-butyl dicarbonate was added. After stirring overnight, the mixture was concentrated and the product was purified on a silica gel column to afford 3.72 g of the desired product as a white solid. 1H NMR (CDCl₃), δ 0.85 (t, 3H), 1.20 (m, 1H), 1.40 (s, 10H), 2.20 (m, 1H), 2.30 (m, 1H), 2.45 (m, 1H), 2.65 (t, 1H), 2.80 (m, 1H), 3.60 (q, 2H), 4.20 (m, 1H), 4.80 (m, 1H), 7.30 (s, 5H).

Step 4g. (3S,4S)-3-BOC-amino-4-ethyl-pyrrolidine

A sample of the compound from step 4f is dissolved in ethanol and treated with 4 atm of H₂ over Pd/C for 24 hours. The deprotected compound is not stored, but is taken directly to the condensation step illustrated in, for example, Example 3, step f.

EXAMPLE 5

(3S,4R-)-3-BOC-amino-4-ethyl-pyrrolidine

Step 5a. E-2-butene-1,4-diol

LAH (25 g) was added to dry Et₂O (1L) under a good nitrogen flow, and the mixture was cooled to −10° C. 2-butyne-1,4-diol (35 g dissolved in 200 mL of dry THF) was added dropwise while the reaction temperature was maintained at −10° C. Upon completion of the addition, the temperature was allowed to warm to 0° C. The reaction mixture was then heated to reflux for 15 hours. The mixture was cooled to −10° to 0° C. and 25 mL of water were added dropwise while the mixture was vigorously stirred. 25 mL of a 15% NaOH solution were then added dropwise with continued stirring, followed by an additional 75 mL of H₂O. The resulting white solid was removed by filtration and washed with 1L of DME. The filtrate, including the DME wash solution, was concentrated in vacuo to afford 31 g of the title product.

Step 5b. E-4-Benzyloxy-2-butene-1-ol

NaH (11.5 g of a 60% dispersion in mineral oil) was placed in a 2L, 3-neck flask equipped with a dropping funnel and nitrogen inlet. The NaH was rinsed with hexane (3×30 mL), and 1L of dry THF was added with a good nitrogen flow. The mixture was then cooled to −10° C. E-1,4-hydroxy-2-butene (32.94 g, 0.379 mol) was dissolved in 200 mL of dry THF. The THF mixture was added dropwise while maintaining the reaction temperature at −10° C. The reaction was allowed to reach room temperature while being stirred for 1 hour. Bu₄NI (1.0 g) was added, then BnBr (34.2 mL, 0.288 mol) was added via syringe over 5 minutes. The mixture was refluxed for 12 hours, then allowed to cool to room temperature. THF was removed by rotary evaporation, and 500 mL of Et₂O and 100 mL of H₂O were added. The layers were separated. The organic layer was then washed with water (1×50 mL) and brine (1×50 mL), dried over MgSO₄, filtered, concentrated and column chromatographed to afford 20.3 g the title compound. MS 196 (M+NH₄)⁺. ¹H NMR δ 4.03–4.07 (m, 2H), 4.15–4.21 (m, 2H), 4.53 (s, 2H), 5.80–5.99 (m, 2H), 7.25–7.38 (m, 5H).

Step 5c. (2S,3S)-[(benzyloxymethyl)oxirane-2-methanol

L-(+)-Diethyl tartrate dissolved in 25 mL of dry CH₂Cl₂ was slowly added to a stirred solution of titanium isopropoxide in 800 mL of dry CH₂Cl₂ at −23° C. under a nitrogen atmosphere. The mixture was stirred for 15 minutes. E-1-Benzyloxy-4-hydroxy-2-butene (17.8 g dissolved in 100 mL of dry CH₂Cl₂) was added dropwise through a dropping funnel. t-BuOOH (41.2 mL of a 5.0–6.0M solution in decane) was then added at about −23° to −30° C., and the mixture was stored overnight at −25° C. The reaction mixture was stirred for 7.5 hours at −23° to −30° C., and Me₂S (2 mL) and 10% aqueous tartaric acid solution (100 mL) were added. The mixture was stirred for 30 minutes, then allowed to reach room temperature and stirred for an additional 1.5 hours. The mixture was poured into a separatory funnel, and the layers were separated. The organic layer was washed with H₂O (2×100 mL) and brine (1×100 mL). The combined aqueous layers were then extracted with CH₂Cl₂. The combined organic layers were then dried over MgSO₄, concentrated by rotary evaporation, and column chromatographed to afford the title compound in 83% yield (16.1 g). MS 212 (M+NH₄)⁺.¹H NMR δ 1.61 (dd, 1H), 3.12 (ddd, 1H), 3.25 (ddd, 1H), 3.54 (dd, 1H), 3.66 (ddd, 1H), 3.78 (dd, 1H), 3.95 (ddd, 1H), 4.58 (AB q, 2H), 7.26–7.40 (m, 5H).

Step 5d. (2R,3R)-2-ethyl-4-benzyloxybutan-,1,3-diol 3.77 g of CuCN and 1.2L of dry Et₂O were placed in an oven-dried flask under a steady flow of nitrogen. The mixture was cooled to −50° C. 377 mL of 1.0 M EtMgBr in THF was add via cannula. The reaction mixture was stirred for 15 minutes to allow the reaction temperature to again reach −50° C. (2S,3R)-3-[[(benzyloxy]oxirane-2-methanol (24.4 g) dissolved in 400 mL of dry Et₂O was added via syringe at a rate which allowed the reaction mixture to be maintained below −50° C. The reaction mixture was stirred for 2 hours while the temperature was maintained between -54° and -49° C. Over the next hour the reaction temperature was maintained at approximately -40° C. Following that, the temperature was maintained at about -30° C. for one hour. During the next 4 hours the temperature was maintained between -36° and -25° C. After this, the temperature was allowed to reach 0° C. over the next 2 hours. Aqueous solutions of $NH_4OH$ and $NH_4Cl$ were added to quench the reaction. The solution was poured into a separatory funnel and the layers separated. The organic layer was washed with $H_2O$ and brine. The original aqueous layer was then extracted with EtOAc. The EtOAc layer was washed with $H_2O$ and brine and was then combined with the earlier organic layer. The combined organic layers were then dried over $MgSO_4$, filtered and concentrated to afford 24.14 g of a mixture of the desired compound, the starting material and the 3-position ring-opened product. MS 242 $(M+NH_4)^+$.$^1$H NMR δ 0.93 (t, 3H), 1.33–1.48 (m, 3H), 2.78 (d, 1H), 2.86 (t, 1H), 3.47–3.95 (m, 5H), 4.58 (s, 2H), 7.27–7.42 (m, 5H).

This mixture was dissolved in 300 mL of a 2:1 mixture of $THF/H_2O$. The reaction flask was placed in a water bath at room temperature to maintain the reaction temperature during the addition of 6.02 g of $NaIO_4$ over a 5 minute period. After stirring for 45 minutes, the water bath was removed and the reaction was stirred overnight. The THF was then removed by rotary evaporation. EtOAc and brine were then added, and the layers were separated. The combined aqueous layers were extracted with EtOAc. The combined organic layers were then dried over $MgSO_4$, filtered, concentrated, and column chromatographed to afford 14.56 g of the title compound.

Step 5e. (2R,3R)-2-ethylbutan-1,3,4-triol

Hydrogenation of (2S,3S)-2-ethyl-3-hydroxy-4-benzyloxy-1-butanol (14.56 g, from step 5d) in 500 mL of EtOH was carried out under 4 atm of $H_2$ for 24 hours at room temperature with 10% Pd/C (7.25 g) catalyst. The catalyst was removed by filtration, and the solvent was removed by rotary evaporation to afford 8.55 g (94%) of the title compound.

Step 5f. (3S,4R)-1-benzyl-4-ethyl-pyrrolidin-3-ol

The compound from step 5e (8.55 g) was dissolved in 50 mL of pyridine. The flask was flushed with nitrogen, maintained under a nitrogen atmosphere and cooled to -40° to -45° C., then methanesulfonyl chloride (9.4 mL) of was added via syringe. The reaction mixture was stirred for 5 hours between -40° and -45° C. $H_2O$ (5 mL) was added, and the mixture was stirred for 15 minutes, then the reaction mixture was allowed to warm to room temperature. Pyridine and $H_2O$ were then removed by rotary evaporation, EtOAc (500 mL) and $H_2O$ (20 mL) were added and the layers were separated. The organic layer was washed with 2M HCl (4×40 mL), dried over $MgSO_4$, filtered and concentrated to afford 16.3 g of a mixture of the desired dimesylate compound and a trimesylate byproduct.

This mixture was dissolved in 200 mL of anhydrous ethanol, and $NaHCO_3$ (28.33 g) and $BnNH_2$ (6.75 mL) were added under nitrogen. The mixture was heated to reflux, stirred for 19 hours, then cooled to room temperature and concentrated. EtOAc (500 mL) and $H_2O$ (400 mL) were then added, and the layers were separated. The organic layer was washed with a saturated solution of $Na_2CO_3$, water and brine. The original aqueous layer was extracted with EtOAc. This EtOAc layer was then washed with a saturated solution of $Na_2CO_3$, water and brine. The combined organic layers were dried over $MgSO_4$, filtered and concentrated to afford 12.02 g of the crude desired product. $^1$H NMR δ 0.93 (t, 3H), 1.30–1.47 (m, 1H), 1.50–1.65 (m, 2H), 1.73 (d, 1H), 1.96–2.11 (m, 1H), 2.23 (t, 1H), 2.62–2.72 (m, 1H), 2.83 (dd, 1H), 3.67 (AB q, 2H), 4.14–4.23 (m, 1H), 7.21–7.27 (m, 3H), 7.32 (d, 2H).

Step 5g. (3S,4R)-1-benzyl-3-BOC-amino-4-ethyl-pyrrolidine

The compound from step 5f is treated according to the procedure of Example 4, step 5, under Mitsunobu Reaction conditions to afford the title compound.

Step 5h. (3S,4R)-3-BOC-amino-4-ethyl-pyrrolidine

A sample of the compound from step 5 g is dissolved in ethanol and treated with 4 atm of $H_2$ over Pd/C for 24 hours. The deprotected compound is not stored, but is taken directly to the condensation step illustrated in, for example, Example 3, step f.

EXAMPLE 6

(3R,4R)-3-BOC-amino-4-methyl-pyrrolidine

Following the procedures of Example 4, except replacing the D-(-)-diisopropyl tartrate of step 4b with L-(+)-diisopropyl tartrate and the ethyl magnesium bromide of step 4c with methyl magnesium bromide, the title compound is prepared.

EXAMPLE 7

(3R,4S)-3-BOC-amino-4-butyl-pyrrolidine

Following the procedures of Example 5, except replacing the L-(+)-diethyl tartrate of step 5c with D-(-)-diethyl tartrate and the ethyl magnesium bromide of step 5d with n-butyl magnesium bromide, the title compound is prepared.

EXAMPLE 8

(3S,4S)-3-trifluoroacetylamino-4-methyl-pyrrolidine

Following the procedures of Example 4, except replacing the di-t-butyl dicarbonate of step 4f with trifluoroacetyl anhydride, the title compound is prepared.

EXAMPLE 9

(3S,4S)-3-methylamino-4-methyl-pyrrolidine

Following the procedures of Example 4, except replacing the di-t-butyl dicarbonate of step 4f with methyl iodide, the title compound is prepared.

EXAMPLE 10

(3S ,4S)-3-hexylamino-4-methyl-pyrrolidine

Following the procedures of Example 4, except replacing the di-t-butyl dicarbonate of step 4f with hexanal in the presence of $K_2CO_3$ followed by reduction with of the imine with $NaCNBH_3$, the title compound is prepared.

EXAMPLE 11

(3S ,4S)-3-BOC-amino-4-methyl-pyrrolidine

Following the procedures of Example 4, except replacing the ethyl magnesium bromide of step 4c with methyl magnesium iodide, the title compound is prepared.

EXAMPLE 12

(3S ,4S)-3-BOC-amino-4-propyl-pyrrolidine

Following the procedures of Example 4, except replacing the ethyl magnesium bromide of step 4c with propyl magnesium iodide, the title compound is prepared.

EXAMPLE 13

(3S,4S)-3-BOC-amino-4-hexyl-pyrrolidine

Following the procedures of Example 4, except replacing the ethyl magnesium bromide of step 4c with n-hexyl magnesium bromide, the title compound is prepared.

EXAMPLE 14

(3S,4S)-3-BOC-amino-4-vinyl-pyrrolidine

Following the procedures of Example 4, except replacing the ethyl magnesium bromide of step 4c with vinyl magnesium chloride, the title compound is prepared.

EXAMPLE 15

(3S,4S)-3-BOC-amino-4-(2-hexenyl)-pyrrolidine

Following the procedures of Example 4, except replacing the ethyl magnesium bromide of step 4c with hex-2-en-1-yl magnesium bromide, the title compound is prepared.

EXAMPLE 16

(3S,4S)-3-BOC-amino-4-ethynyl-pyrrolidine

Following the procedures of Example 4, except replacing the ethyl magnesium bromide of step 4c with ethynyl magnesium bromide, the title compound is prepared.

EXAMPLE 17

(3S,4S)-3-BOC-amino-4-(but-2-yn-1-yl)-pyrrolidine

Following the procedures of Example 4, except replacing the ethyl magnesium bromide of step 4c with but-2-yn-1-yl magnesium bromide, the title compound is prepared.

EXAMPLE 18

(3S,4S)-3-BOC-amino-4-cyclopropyl-pyrrolidine

Following the procedures of Example 4, except replacing the ethyl magnesium bromide of step 4c with cyclopropyl magnesium bromide, the title compound is prepared.

EXAMPLE 19

(3S,4S)-3-BOC-amino-4-cyclobutyl-pyrrolidine

Following the procedures of Example 4, except replacing the ethyl magnesium bromide of step 4c with cyclobutyl magnesium bromide, the title compound is prepared.

EXAMPLE 20

(3S,4S)-3-BOC-amino-4-cyclopentyl-pyrrolidine

Following the procedures of Example 4, except replacing the ethyl magnesium bromide of step 4c with cyclopentyl magnesium bromide, the title compound is prepared.

EXAMPLE 21

(3S,4S)-3-BOC-amino-4-cyclohexyl-pyrrolidine

Following the procedures of Example 4, except replacing the ethyl magnesium bromide of step 4c with cyclohexyl magnesium bromide, the title compound is prepared.

EXAMPLE 22

Preparation of cis-2,8-diaza-8-BOC-bicyclo[4.3.0] nonane

Step 22a. (2S,3R)-1-bromobenzyloxy-3-hydroxymethyl-hex-5-en-2-ol

To a stirred suspension of CuCN in dry $Et_2O$ under nitrogen at −50° C. is added allyl magnesium bromide. The resulting suspension is stirred for 30 minutes, then (2R,3S)-3[[-bromobenzyl)oxy]methyl]oxirane-2-methanol (from Example 4, step b) is slowly added. The reaction is stirred at −30° C. and then 0° C. until the reaction is complete. Aqueous solutions of $NH_4OH$ and $NH_4Cl$ are added, and the mixture is extracted with ether. The organic extract is washed with saturated NaCl, dried over $MgSO_4$, and filtered, and the solvent is evaporated to afford the desired intermediate. The intermediate is dissolved in THF—$H_2O$ and $NaIO_4$ is added to the solution, and the mixture is stirred at room temperature for 4 hours. The THF is removed by rotary evaporation. Ethyl acetate and brine are then added, the layers are separated, and the organic layer is dried over $MgSO_4$, filtered, concentrated, and column chromatographed to afford the title compound.

Step 22b. (2R,3S)-3-hydroxymethyl-hex-5-en-1,2-diol

The compound prepared from step 22a is deprotected with sodium/ammonia to afford the desired product.

Step 22c. (2R,3S)-1-methanesulfonyloxy-3-(methanesulfonyloxy)methyl-hex-5-en-2-ol To a solution of the product from step 22b in pyridine cooled to −40° C. is added MsCl slowly via syringe. The mixture is stirred for 4 hours at −40° C., then is quenched with water and allowed to warm to room temperature. The solvent is removed, the residue is taken up in ethyl acetate, the solution is washed with water, 2M HCl, $NaHCO_3$ and brine, then is dried over $MgSO_4$. The solution is filtered and concentrated to afford the desired dimesylate compound.

Step 22d. (3R,4S)-4-allyl-1-benzylpyrrolidin-3-ol

The dimesylate compound from step 22c is dissolved in absolute EtOH and treated with benzyl amine at reflux in the presence of $NaHCO_3$ under $N_2$. After cooling, the solvent is removed under vacuum, and the residue is redissolved, washed and dried. The solvent is removed to give the title compound.

Step 22e. (3S,4S)-4-allyl-1-benzyl-pyrrolidin-3-amine

The compound from step 22d is treated under Mitsunobu Reaction conditions with $Ph_3P$, DEAD, and phthalylamine, followed by treatment with hydrazine. The title compound is obtained by extraction from the reaction mixture.

Step 22f (3S,4S)-4-allyl-1-benzyl-3-BOC-aminopyrrolidine

The compound from step 22e is treated with di-t-butyl dicarbonate in methylene chloride. The title compound is obtained by extraction from the reaction mixture.

Step 22g. (3S,4S)-4-(3-hydroxypropyl)-1-benzyl-3-BOC-aminopyrrolidine

The compound from step 22f is treated with $BH_3$ and $H_2O_2$ in aqueous NaOH. The title compound is obtained by extraction from the reaction mixture.

Step 22h. (3S,4S)-4-(3-methanesulfonyl-oxypropyl)-1-benzyl-3-BOC-aminopyrrolidine The compound from step 22g is treated with methanesulfonyl chloride in methylene chloride. The title compound is obtained by extraction from the reaction mixture.

Step 22i. cis-2,8-diaza-2-benzyl-bicyclo[4.3.0]nonane

The compound from step 22e is treated with NaH under anhydrous conditions in THF. The title compound is obtained by extraction from the reaction mixture.

Step 22j. cis-2,8-diaza-2-benzyl-8-BOC-bicyclo[4.3.0] nonane

The compound from step 22f is treated with di-t-butyl dicarbonate, and the title compound is obtained by extraction from the reaction mixture.

Step 22k. cis-2,8-diaza-8-BOC-bicyclo[4.3.0]nonane

The compound from step 22g is treated with H$_2$ over Pd/C in ethanol, and the title compound is obtained by extraction from the reaction mixture.

EXAMPLE 23

Preparation of trans-2,8-diaza-8-BOC-8-bicyclo[4.3.0]nonane

Step 23a. (2R,3R)-1-bromobenzyloxy-3-hydroxymethyl-hex-5-en-2-ol

To a stirred suspension of CuCN in dry Et$_2$O under nitrogen at −50° C. is added allyl magnesium bromide. The resulting suspension is stirred for 30 minutes, then (2S,3S)-3-[[4-bromobenzyl)oxy]methyl]oxirane-2-methanol (from Example 5, step b) is slowly added. The reaction is stirred at −30° C. and then 0° C. until the reaction is complete. Aqueous solutions of NH$_4$OH and NH$_4$Cl are added, and the mixture is extracted with ether. The organic extract is washed with saturated NaCl, dried over MgSO$_4$, and filtered, and the solvent is evaporated to afford the desired intermediate. The intermediate is dissolved in THF—H$_2$O and NaIO$_4$ is added to the solution, and the mixture is stirred at room temperature for 4 hours. The THF is removed by rotary evaporation. Ethyl acetate and brine are then added, the layers are separated, and the organic layer is dried over MgSO$_4$, filtered, concentrated, and column chromatographed to afford the title compound.

Step23b. (2R,3R)-3-hydroxymethyl-hex-5-en-1,2-diol

The compound prepared from step 23a is deprotected with sodium/ammonia to afford the desired product.

Step 23c. (2R,3R)-1-methanesulfonyloxy-3-(methanesulfonyloxy)methyl-hex-5-en-2-ol To a solution of the product from step 23b in pyridine cooled to −40° C. is added MsCl slowly via syringe. The mixture is stirred for 4 hours at −40° C., then is quenched with water and allowed to warm to room temperature. The solvent is removed, the residue is taken up in ethyl acetate, the solution is washed with water, 2M HCl, NaHCO$_3$ and brine, then is dried over MgSO$_4$. The solution is filtered and concentrated to afford the desired dimesylate compound.

Step 23d. (3R,4R)-4-allyl-1-benzylpyrrolidin-3-ol

The dimesylate compound from step 23c is dissolved in absolute EtOH and treated with benzyl amine at reflux in the presence of NaHCO$_3$ under N$_2$. After cooling, the solvent is removed under vacuum, and the residue is redissolved, washed and dried. The solvent is removed to give the title compound.

Step 23e. (3S,4R)-4-allyl-1-benzyl-pyrrolidin-3-amine

The compound from step 23d is treated under Mitsunobu Reaction conditions with Ph$_3$P, DEAD, and phthalylamine, followed by treatment with hydrazine. The title compound is obtained by extraction from the reaction mixture.

Step 23f. (3S,4R)-4-allyl-1-benzyl-3-BOC-aminopyrrolidine

The compound from step 23e is treated with di-t-butyl dicarbonate in methylene chloride. The title compound is obtained by extraction from the reaction mixture.

Step 23 g. (3S,4R)-4-(3-hydroxypropyl)-1-benzyl-3-BOC-aminopyrrolidine

The compound from step 23f is treated with BH$_3$ and H$_2$O$_2$ in aqueous NaOH. The title compound is obtained by extraction from the reaction mixture.

Step 23h. (3S,4R)-(3-methanesulfonyloxypropyl)-1-benzyl-3-BOC-aminopyrrolidine

The compound from step 23g is treated with methanesulfonyl chloride in methylene chloride. The title compound is obtained by extraction from the reaction mixture.

Step 23i. trans-2,8-diaza-2-benzyl-8-bicyclo[4.3.0]nonane

The compound from step 23e is treated with NaH under anhydrous conditions in THF. The title compound is obtained by extraction from the reaction mixture.

Step 23j. trans-2,8-diaza-2-benzyl-8-BOC-8-bicyclo[4.3.0]nonane

The compound from step 23f is treated with di-t-butyl dicarbonate, and the title compound is obtained by extraction from the reaction mixture.

Step 23k. trans-2,8-diaza-8-BOC-bicyclo[4.3.0]nonane

The compound from step 23g is treated with H$_2$ over Pd/C in ethanol, and the title compound is obtained by extraction from the reaction mixture.

EXAMPLE 24

Preparation of cis-2,7-diaza-7-BOC-bicyclo[3.3.0]octane

Following the procedures of Example 22, except replacing the allyl magnesium bromide of step 22a with vinyl magnesium bromide, and carrying the product forward, the title compound is prepared.

EXAMPLE 25

Preparation of cis-2,9-diaza-9-BOC-bicyclo[5.3.0]decane

Following the procedures of Example 22, except replacing the allyl magnesium bromide of step 22a with hex-1-en-4-yl magnesium bromide, and carrying the product forward, the title compound is prepared.

EXAMPLE 26

In Vitro Assay of Antibacterial Activity

The in vitro antibacterial activity of the illustrative compounds was demonstrated as follows: Minimum inhibitory concentrations (MICs) were determined by the agar dilution method, in which twelve petri dishes were prepared, each containing successive aqueous 2-fold dilutions of the test compounds mixed with 10 mL of sterilized Brain Heart Infusion (BHI) agar. Each plate was inoculated with 1:100 (or 1:10 for slow-growing strains, primarily Micrococcus and Streptococcus) dilutions of up to 32 different microorganisms, using a Steers replicator block calibrated to deliver approximately 104 colony forming units (CFUs). The inoculated plates were incubated at from about 35° C. to about 37° C. for approximately 20–24 hours. In addition, a control plate using BHI agar containing no test compound was prepared and incubated at the beginning and at the end of each test. The quinolone antibacterial ciprofloxacin was used as a control ("Cntl").

After incubation, each petri dish was observed for the presence or absence of microorganism growth. The MIC was defined as the lowest concentration of test compound yielding no growth (a slight haze or sparsely isolated colonies at the inoculum spot) as compared to the growth control containing no test compound.

The results of the above tests, shown in Table 1 below, demonstrate that the illustrative compounds are surprisingly effective in combating bacterial growth.

TABLE 1

In Vitro Antibacterial Activity (MIC Values in µg/mL)

| Organism | Ex. 1 | Ex. 2 | Ex. 3 | Control |
|---|---|---|---|---|
| Staph. aureus ATCC 6538P | 0.01 | 0.02 | 0.01 | 0.05 |
| Staph. aureus A5177 | 0.02 | 0.02 | 0.02 | 0.39 |
| Staph. aureus 5278 | 0.01 | 0.05 | 0.02 | 0.39 |
| Staph. aureus 642A | 0.02 | 0.02 | 0.02 | 0.39 |
| Staph. aureus NCTC10649M | 0.01 | — | 0.01 | 0.39 |
| Staph. aureus CMX 553 | 0.05 | 0.02 | 0.02 | 0.78 |
| Staph. aureus 1775 Cipro. R. | 0.39 | 0.78 | 0.78 | >100 |
| Staph. epidermidis 3519 | 0.02 | 0.05 | 0.02 | 0.39 |
| Entero. faecium ATCC 8043 | 0.1 | 0.05 | 0.1 | 0.78 |
| Strep. bovis A5169 | 0.05 | 0.1 | 0.1 | 1.56 |
| Strep. agalactiae CMX 508 | 0.05 | 0.02 | 0.1 | 0.78 |
| Strep. pyogenes EES61 | 0.05 | 0.02 | 0.1 | 0.39 |
| Strep. pyogenes 930 CONST | 0.05 | 0.05 | 0.05 | 0.78 |
| Strep. pyogenes 2548 INDUC | 0.02 | 0.05 | 0.05 | 0.39 |
| M. luteus ATCC 9341 | 0.1 | 0.05 | 0.1 | 3.1 |
| M. luteus ATCC 4698 | 0.1 | 0.05 | 0.1 | 1.56 |
| Escherichia coli Juhl | 0.005 | 0.01 | 0.02 | 0.05 |
| E. coli SS | 0.002 | 0.001 | 0.002 | 0.005 |
| E. coli DC-2 | 0.05 | 0.1 | 0.2 | 0.2 |
| E. coli H560 | 0.005 | 0.01 | 0.01 | 0.01 |
| E. coli KNK 437 | 0.05 | 0.1 | 0.1 | 0.2 |
| Enter. aerogenes ATCC 13048 | 0.02 | 0.1 | 0.05 | 0.05 |
| Klebs. pneumoniae ATCC8045 | 0.01 | 0.05 | 0.02 | 0.01 |
| Providencia stuartii CMX 640 | 0.39 | 0.39 | 0.78 | 0.78 |
| P. aeruginosa BMH 10 | 0.1 | 0.2 | 0.39 | 0.1 |
| P. aeruginosa A5007 | 0.2 | 0.39 | 0.39 | 0.2 |
| P. aeruginosa K799/WT | 0.2 | 0.78 | 0.39 | 0.1 |
| P. aeruginosa K799/61 | 0.02 | 0.1 | 0.02 | 0.02 |
| Pseudomonas cepacia 2961 | 0.78 | 1.56 | 0.78 | 3.1 |
| Acinetob. calcoaceticus CMX 669 | 0.02 | 0.05 | 0.02 | 0.39 |
| P. aeruginosa 5263 | 3.1 | 3.1 | 3.1 | 12.5 |
| P. aeruginosa 2862 | 3.1 | 6.2 | 3.1 | 12.5 |
| Candida albicans CCH 442 | >100 | >100 | >100 | >100 |
| Myco. smegmatis ATCC 114 | 0.02 | 0.02 | 0.02 | 1.56 |
| Nocardia asteroides ATCC 9970 | 3.1 | 0.78 | 0.39 | 25 |

What is claimed is:

1. A process for the preparation of chiral 3-aminopyrrolidine compounds having the formula:

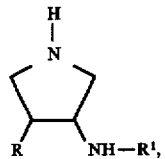

wherein R is $C_1-C_6$-alkyl, $C_2-C_6$-alkenyl, $C_2-C_6$-alkynyl, or $C_3-C_6$-cycloalkyl, and $R^1$ is hydrogen, $C_1-C_6$-alkyl or an amino-protecting group;

comprising:

(a) protecting a single hydroxyl group of selected positional isomer of 2-butene-1,4-diol, by stepwise treatment with a base, an arylmethyl halide and a tetraalkylammonium halide, and isolating a monoprotected hydroxy-olefin having the formula:

HO—CH₂—CH=CH—CH₂—OAr, wherein Ar represents the aryl moiety;

(b) chirally oxidizing the monoprotected hydroxy-olefin with titanium isopropoxide, an optically active chiral tartrate ester and t-butyl hydroperoxide, and isolating an epoxy compound having the formula:

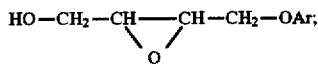

(c) reacting the epoxy compound with an R—Mg—X compound, wherein R is as defined above, and X is halogen, under Grignard Reaction conditions, and isolating the chiral third intermediate compound having the formula:

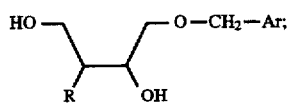

(d) removing the protecting group from the chiral third intermediate compound, and isolating the chiral fourth intermediate compound having the formula:

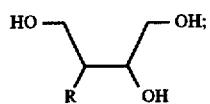

(e) sulfonylating the chiral fourth intermediate compound by treatment with a substituted sulfonyl chloride, and isolating the chiral diprotected triol compound having the formula:

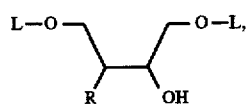

wherein L represents the substituted sulfonyl moiety;

(f) cyclizing the chiral diprotected triol compound by treatment with an arylmethylamine compound, and isolating the chiral pyrrolidine intermediate having the formula:

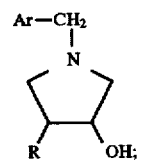

(g) replacing the hydroxyl group of the chiral pyrrolidine intermediate with an amino group by an amination reaction that inverts the chiral center, and isolating the chiral aminopyrrolidine compound having the formula:

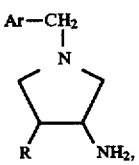

(h) derivatizing the amino group of the chiral aminopyrrolidine compound, and isolating the chiral substituted-aminopyrrolidine compound having the formula:

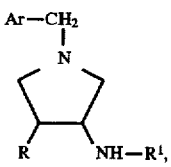

wherein R¹ is as defined above;

(i) deprotecting the ring nitrogen of the chiral substituted-aminopyrrolidine compound, and isolating the desired product.

2. A process according to claim 1 wherein in step (a) the 2-butene-1,4-diol is the cis isomer; in step (b), the optically active chiral tartrate ester is D-(−)-diisopropyl tartrate; and the product has the cis-3S,4S-configuration.

3. A process according to claim 1 wherein in step (a) the 2-butene-1,4-diol is the cis isomer; in step (b), the optically active chiral tartrate ester is L-(+)-diisopropyl tartrate; and the product has the cis-3R,4R-configuration.

4. A process according to claim 1 wherein in step (a) the 2-butene-1,4-diol is the trans-isomer; in step (b), the optically active chiral tartrate ester is D-(−)-diiso-propyl tartrate; and the product has the trans-3R,4S-configuration.

5. A process according to claim 1 wherein in step (a) the 2-butene-1,4-diol is the trans isomer; in step (b), the optically active chiral tartrate ester is L-(+)-diisopropyl tartrate; and the product has the trans-3S,4R-configuration.

6. A process according to claim 1, wherein R¹ is t-butyloxycarbonyl and in step (a) the 2-butene-1,4-diol is treated with one equivalent of NaH in an aprotic polar organic solvent at from −20° C. to 5° C. under an inert atmosphere and anhydrous conditions, and the arylmethyl halide of the subsequent reaction, performed at ambient temperature for 8 to 24 hours, is selected from the group consisting of benzyl bromide, benzyl chloride, benzyl iodide, 4-bromobenzyl bromide, and 4-chlorobenzyl bromide; in step (b), the first intermediate compound is reacted with titanium isopropoxide, an optically active chiral tartrate ester and tert-butyl hydroperoxide in dry methylene chloride in the presence of 4 Å molecular sieves at −40° C. to −20° C. for 0.5 to 24 hours; in step (c) the Grignard reaction is performed with a CuCN catalyst at −78° to −20° C., followed by treatment of the intermediate with NaIO₄ at ambient temperature in aqueous THF; in step (d) the protecting group is removed from the chiral third intermediate compound by hydrogenolysis over Pd/C in an alcoholic solution; in step (e) the fourth intermediate compound (5) is sulfonylated with methanesulfonyl chloride; in step (f) the chiral diprotected triol compound (6) is cyclized with benzylamine in an alcoholic solution and in the presence of a base at 80° C.–120° C.; in step (g) the hydroxyl group of the chiral pyrrolidine intermediate is replaced by treatment with triphenylphosphine, diethylazodicarboxylate, and phthalylamine, followed by treatment with hydrazine in ethanol; in step (h), the seventh intermediate compound is derivatized by treatment with di-t-butyldicarbonate; and in step (i), the ring nitrogen of the chiral substituted-aminopyrrolidine compound is deprotected by hydrogenolysis over Pd/C in an alcoholic solution.

7. A process according to claim 6 wherein R is C₁–C₆-alkyl.

8. A process according to claim 7 wherein R is ethyl.

* * * * *